US009624484B2

(12) United States Patent
Georgiou et al.

(10) Patent No.: US 9,624,484 B2
(45) Date of Patent: Apr. 18, 2017

(54) ENGINEERED PRIMATE L-METHIONINASE FOR THERAPEUTIC PURPOSES

(71) Applicant: Board of Regents, The University of Texas System, Austin, TX (US)

(72) Inventors: George Georgiou, Austin, TX (US); Everett Stone, Austin, TX (US); Wei-Cheng Lu, Austin, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 15/297,102

(22) Filed: Oct. 18, 2016

(65) Prior Publication Data

US 2017/0044514 A1 Feb. 16, 2017

Related U.S. Application Data

(62) Division of application No. 14/472,750, filed on Aug. 29, 2014, now Pat. No. 9,481,877.

(Continued)

(51) Int. Cl.

| | |
|---|---|
| ***C12N 9/88*** | (2006.01) |
| ***C12N 15/79*** | (2006.01) |
| ***C12N 1/20*** | (2006.01) |
| ***A61K 38/51*** | (2006.01) |
| ***C12N 15/74*** | (2006.01) |
| ***C12N 15/70*** | (2006.01) |
| ***A61K 45/06*** | (2006.01) |

(Continued)

(52) U.S. Cl.

CPC ................ *C12N 9/88* (2013.01); *A61K 35/12* (2013.01); *A61K 38/51* (2013.01); *A61K 45/06* (2013.01); *C12N 1/14* (2013.01); *C12N 1/20* (2013.01); *C12N 5/0601* (2013.01); *C12N 15/70* (2013.01); *C12N 15/74* (2013.01); *C12N 15/79* (2013.01); *C12Y 404/01001* (2013.01)

(58) Field of Classification Search

None

See application file for complete search history.

(56) References Cited

U.S. PATENT DOCUMENTS

| | | | |
|---|---|---|---|
| 5,889,155 | A | 3/1999 | Ashkenazi et al. |
| 8,709,407 | B2 | 4/2014 | Georgiou |

(Continued)

FOREIGN PATENT DOCUMENTS

| | | |
|---|---|---|
| WO | WO2011/097381 | 8/2011 |

OTHER PUBLICATIONS

"cystathionine gamma-lyase [Rattus norvegicus]" Genbank ID No. BAB19922.2, Apr. 20, 2001.

(Continued)

*Primary Examiner* — Robert Mondesi
*Assistant Examiner* — Richard Ekstrom
(74) *Attorney, Agent, or Firm* — Parker Highlander, PLLC

(57) ABSTRACT

Methods and compositions relating to the engineering of an improved protein with methionine-γ-lyase enzyme activity are described. For example, in certain aspects there may be disclosed a modified cystathionine-γ-lyase (CGL) comprising one or more amino acid substitutions and capable of degrading methionine. Furthermore, certain aspects of the invention provide compositions and methods for the treatment of cancer with methionine depletion using the disclosed proteins or nucleic acids.

12 Claims, 5 Drawing Sheets

Related U.S. Application Data

(60) Provisional application No. 61/871,768, filed on Aug. 29, 2013.

(51) Int. Cl.

| | |
|---|---|
| ***C12N 1/14*** | (2006.01) |
| ***C12N 5/07*** | (2010.01) |
| ***A61K 35/12*** | (2015.01) |

(56) References Cited

U.S. PATENT DOCUMENTS

| | | | |
|---|---|---|---|
| 9,481,877 B2 * | 11/2016 | Georgiou | C12N 9/88 |
| 2005/0036984 A1 | 2/2005 | Harrison et al. | |
| 2006/0107342 A1 | 5/2006 | Amir | |
| 2009/0304666 A1 | 12/2009 | Harrison et al. | |
| 2011/0200576 A1 | 8/2011 | Georgiou | |
| 2012/0156672 A1 | 6/2012 | Otte et al. | |
| 2014/0287484 A1 | 9/2014 | Georgiou | |

OTHER PUBLICATIONS

"cystathionine gamma-lyase homolog [imported]—Stenotrophomonas maltophilia" Genbank ID No. T45483, Jan. 31, 2000.
"hypothetical protein [Pongo abelii]" Genbank ID No. CAH89476.1, May 1, 2008.
"Macaca fascicularis" Genbank ID No. AAW71993, Jan. 7, 2005.
"Pan troglodytes" Genbank ID No. XP_513486, May 13, 2011.
"Pongo abelii" Genbank ID No. NP_001124635, Mar. 10, 2011.
"probable cystathionine gamma-lyase PA0400 [imported]—Pseudomonas aeruginosa" Genbank ID No. F83595, Sep. 15, 2000.
Ashe et al., "N5-methyltetrahydrofolate: homocysteine methyltransferase activity in extracts from normal, malignant and embryonic tissue culture cells," *Biochem. Biophys. Res. Commun.*, 57:417-425, 1974.
Breillout et al., In: *Methionine dependency of malignant tumors: a possible approach for therapy*, Oxford University Press, 1628-1632, 1990.
Breitinger et al., "The three-dimensional structure of cystathionine β-lyase from Arabidopsis and its substrate specificity," *Plant Physiology*, 126:631-642, 2001.
Esaki and Soda, "L-methionine gamma-lyase from *Pseudomonas putida* and *Aeromonas," Methods Enzymol.*, 143:459-465, 1987.
Glode et al., "Cysteine auxotrophy of human leukemic lymphoblasts is associated with decreased amounts of intracellular cystathionase protein," *Biochemistry*, 20(5):1306-1311, 1981.
Halpern et al., "The effect of replacement of methionine by homocystine on survival of malignant and normal adult mammalian cells in culture," Proc. Natl. Acad. Sci. USA, 71:1133-1136, 1974.
Hori et al., "Gene cloning and characterization of Pseudomonas putida L-methionine-alphadeamino-gamma-mercaptomethane-lyase," *Cancer Res.*, 56:2116-2122, 1996.
Huang et al., "Site-directed mutagenesis on human cystathionine-gamma-lyase reveals insights into the modulation of H2S production," *Journal of Molecular Biology*, 396(3):708718, 2009.
International Search Report and Written Opinion issued in International Application No. PCT/US2014/053374, mailed Jan. 14, 2015.
International Search Report and Written Opinion issued in International Application No. PCT/US2014/053359, mailed Mar. 23, 2015.
International Search Report and Written Opinion, issued in PCT/US2011/023606, dated Oct. 25, 2011.
Invitation to Pay Additional Fees issued in International Application No. PCT/US2014/053359, mailed Jan. 16, 2015.
Ito et al., "Purification and characterization of methioninase from *Pseudomonas putida," J. Biochem.*, 79:1263-1272, 1976.
Kim et al., "Expression of cystathionine β-synthase is downregulated in hepatocellular carcinoma and associated with poor prognosis," *Oncology Reports*, 21(6):1449-1454, 2009.
Kraus et al., "Cystathionine γ-lyase: clinical, metabolic, genetic, and structural studies," *Mol. Genet. Metab.*, 97:250-259, 2009.
Kreis and Goodenow, "Methionine cultures of selected rodent and 2262, 1978. requirement and replacement human malignant and normal by homocysteine in tissue cells," *Cancer Res.*, 38:2259-2262, 1978.
Kreis et al., "Effect of nutritional and enzymatic methionine deprivation upon human normal and malignant cells in tissue culture," *Cancer Res.*, 40:634-641, 1980.
Kreis, "Tumor therapy by deprivation of L-methionine: rationale and results," *Cancer Treatment Rpts.*, 63:1069-1072, 1979.
Kudou et al., "Structure of the antitumour enzyme L-methionine gamma-lyase from Pseudomonas putida at 1.8 A resolution," *J. Biochem.*, 141:535-544, 2007.
Link et al., "Cystathionase: a potential cytoplasmic marker of hematopoietic differentiation". *Blut*, 47(1):31-39, 1983.
Lishko et al., "Depletion of serum methionine by methioninase in mice," *Anticancer Res.*, 13:1465-1468, 1993.
Liu et al., "Methionine dependency and the therapy of tumor," *Parenteral and Enteral Nutrition*, 12(4): 247-250, 2005. (English Abstract).
Lu et al., "Cloning and nucleotide sequence of human liver cDNA encoding for cystathionine gamma-lyase," *Biochem. Biophys. Res. Commun.*, 189:749-758, 1992 (Abstract only).
Lu, "Evolved enzymes for cancer therapeutics and orthogonal system," *Dissertation—The University of Texas at Austin*, Aug. 2013.
Messerschmidt et al., "Determinants of enzymatic specificity in the Cys-Met-metabolism PLP-dependent enzymes family crystal structure of cystathionine gamma-lyase from yeast and intrafamiliar structure comparison," *Biol. Chem.*, 384:373-386, 2003.
Motoshima et al., "Crystal structure of the pyridoxal 5'-phosphate dependent 1-methionine gamma-lyase from *Pseudomaonas putida*," J. Biochem., 158:349-354, 2000.
Nakayama et al., "Purification of bacterial L-methionine gamma-lyase," *Anal. Biochem.*, 138:421-424, 1984.
Office Communication issued in U.S. Appl. No. 14/472,750, dated Dec. 31, 2015.
Rao et al., "Role of the transsulfuration pathway and of gamma-cystathionase activity in the formation of cysteine and sulfate from methionine in rat hepatocytes," *J. Nutrition*, 120:837845, 1990.
Sato and Nozaki, "Methionine gamma-lyase: the unique reaction mechanism, physiological roles, and therapeutic applications against infectious diseases and cancers," *IUMBM Life*, 61:1019-1028, 2009.
Schellenberger et al., "A recombinant polypeptide extends the in vivo half-life of peptides and proteins in a tunable manner," *Nat. Biotechnol.*, 27:1186-1190, 2009.
Sridhar et al., "Crystallization and preliminary crystallographic characterization of recombinant L-methionine-alpha-deamino-gamma-mercaptomethane lyase (methioninase)," *Acta. Crystall. Section D Biol. Crystall.*, 56:1665-1667, 2000.
Steegborn et al., "Kinetics and inhibition of recombinant human cystathionine gamma-lyase. Toward the rational control of transsulfuration," *J. Biolog. Chem.*, 274:12675-12684, 1999.
Stone et al., "De novo engineering of a human cystathionine-y-lyase for systemic (L)- Methionine depletion cancer therapy," *ACS Chem Biol.*, 7(11):1822-1829, 2012.
Sun et al., "In vivo efficacy of recombinant methioninase is enhanced by the combination of polyethylene glycol conjugation and pyridoxal 5'-phosphate supplementation," *Cancer Research*, 63:8377-8383, 2003.
Tan et al., "Anticancer efficacy of methioninase in vivo," *Anticancer Res.*, 16:3931-3936, 1996.
Tan et al., "Overexpression and large-scale production of recombinant L-methionine-alpha-deamino-gamma-mercaptomethane-lyase for novel anticancer therapy," *Protein Expr. Puri f.*, 9:233-245, 1997.
Tan et al., "Recombinant methioninase infusion reduces the biochemical endpoint of serum methionine with minimal toxicity in high-stage cancer patients," *Anticancer Res.*, 17:3857-3860, 1997.

(56) References Cited

OTHER PUBLICATIONS

Tan et al., "Serum methionine depletion without side effects by methioninase in metastatic breast cancer patients," *Anticancer Res.*, 16:3937-3942, 1996.
Wawrzynczak and Thorpe, In: *Immunoconjugates, Antibody Conjugates In Radioimaging and Therapy of Cancer*, Vogel (Ed.), NY, Oxford University Press, pp. 28-55, 1987.
Yang et al., "PEGylation confers greatly extended half-life and attenuated immunogenicity to recombinant methioninase in primates," *Cancer Research*, 64:6673-6678, 2004.
Yang et al., "Pharmacokinetics, methionine depletion, and antigenicity of recombinant methioninase in primates," *Clinical Cancer Research*, 10:2131-2138, 2004.
Yoshioka et al., "Anticancer efficacy in vivo and in vitro, synergy with 5 -fluorouracil, and safety of recombinant methioninase," *Cancer Res.*, 58:2583-2587, 1998.
Zhang et al., "Stromal control of cysteine metabolism promotes cancer cell survival in chronic lymphocytic leukemia," *Nat Cell Biol.*, 14:276-286, 2012.
Zhao et al., "Frequent Epigenetic Silencing of the Folate-Metabolising Gene Cystathionine-Beta-Synthase in Gastrointestinal Cancer," *PLoS One*, 7(11):e49683, 2012.
Zhu et al., "Kinetic properties of polymorphic variants and pathogenic mutants in human cystathionine γ-lyase," *Biochemistry*, 47:6226-6232, 2008.
"Google Search—wei-cheng lu evolved enzymes for cancer therapeutics and orthogonal system", dated Jan. 18, 2017.
Extended European Search Report issued in European Application No. 14 84 1106, mailed Jan. 30, 2017.

* cited by examiner

ENGINEERED PRIMATE L-METHIONINASE FOR THERAPEUTIC PURPOSES

The present application is a divisional of U.S. application Ser. No. 14/472,750, filed Aug. 29, 2014, which claims the priority benefit of U.S. provisional application No. 61/871,768, filed Aug. 29, 2013, the entire contents of each of which are incorporated herein by reference.

The invention was made with government support under Grant No. R01 CA154754 awarded by the National Institutes of Health. The government has certain rights in the invention.

BACKGROUND OF THE INVENTION

1. Field of the Invention

The present invention relates generally to the fields of medicine and biology. More particularly, it concerns an improved human methionine-γ-lyase (hMGL) for use in the treatment of cancer.

2. Description of Related Art

The demand for the essential amino acid, L-methionine, is exceptionally high in cancerous tissues. Depletion of methionine has been shown to be effective in killing a wide variety of tumor types without adversely affecting non-cancerous tissues. Methionine depletion can be effected via the action of enzymes that hydrolyze the amino acid. While human methionine depleting enzymes did not previously exist, a bacterial enzyme from *Pseudomonas aeruginosa*, methionine-γ-lyase, was shown to be therapeutically effective in the clinic and had been evaluated in clinical trials. However, methionine-γ-lyase, being a bacterial protein, is highly immunogenic, eliciting the formation of specific antibodies, leading to adverse reactions and also reduced activity. Methionine-γ-lyase also has a very short half-life of only about 2 h in vitro and in vivo, necessitating very frequent and impractically high dosing to achieve systemic depletion.

Systemic methionine depletion is the focus of much research and has the potential to treat cancers, such as metastatic breast cancer, prostate, neuroblastoma, and pancreatic carcinoma among others. Although there is much excitement for this therapeutic approach, the bacterially-derived methionine-γ-lyase has serious shortcomings (immunogenicity and rapid deactivation in serum, as discussed above) that greatly dampen enthusiasm for its use as a chemotherapeutic agent.

Previously, an engineered human methionine-γ-lyase (hMGL-NLV) was created by introducing three key amino acid substitutions in the human enzyme cystathionine-γ-lyase (CGL): E59N, R119L, E339V. See, U.S. Pat. No. 8,709,407, which is incorporated herein by reference. Unlike native CGL, which displays essentially no catalytic activity towards L-methionine, the E59N, R119L, E339V variant enzyme (hMGL-NLV) displays robust L-methionine degrading activity in vivo and in vitro. Nonetheless, there remains a need to develop human L-methionine degrading enzymes with higher catalytic activity so that a therapeutic effect can be attained with lower dosing and/or less frequent administration of the enzyme.

SUMMARY OF THE INVENTION

Provided herein are human methionine-γ-lyase (hMGL) mutants with higher catalytic activity than hMGL-NLV. The preferred improved hMGL proteins exhibit 6-10 fold higher activity. Due to the higher catalytic activity, the provided hMGL proteins may display higher therapeutic potency for methionine depletion and thus lower concentrations of therapeutic agent may be required for dosing of patients. This enzyme was engineered by introducing amino acid substitutions in the human enzyme cystathionine-γ-lyase (CGL) at positions comprising residues E59, R119, or E339. In one particular embodiment, preferred substitutions of E59, R119, and E339 in hCGL include, respectively, L-asparagine (at position 59), L-leucine (at position 119) and L-valine (at position 339). The present invention discloses compositions of matter displaying higher catalytic activity relative to the hMGL-NLV variants. These contain substitutions at least at two of the E59, R119, or E339 positions identified as critical for conferring L-methionine-γ-lyase activity compared to the hMGL-NLV variants. The higher catalytic activity of these variants is important because lower concentrations of therapeutic agent may be required for dosing of patients.

The variants having additional amino acid substitutions include SEQ ID NO: 3, hCGL-E59N-S63L-L91M-R119L-K268R-T311G-E339V-I353S (hCGL-8mut-1); SEQ ID NO: 4, hCGL-E59I-S63L-L91M-R119L-K268R-T311G-E339V-I353S (hCGL-8mut-2); SEQ ID NO: 5, hCGL-E59N-S63L-L91M-R119A-K268R-T311G-E339V-I353S (hCGL-8mut-3); and SEQ ID NO: 6, hCGL-E59I-S63L-L91M-R119A-K268R-T311G-E339V-I353S (hCGL-8mut-4).

Certain aspects of the present invention overcome a major deficiency in the art by providing improved enzymes that comprise human polypeptide sequences having methionine-γ-lyase (MGL) activity, which may be suitable for cancer therapy and have low immunogenicity, improved serum stability, and improved catalytic activity. Accordingly, in a first embodiment there is provided a modified polypeptide (i.e., enzyme), particularly an enzyme variant with methionine-degrading activity derived from primate enzymes related to MGL. For example, the novel enzyme variant may have an amino acid sequence selected from the group consisting of SEQ ID NOs: 3-6. In particular, the variant may be derived from human enzymes, such as human cystathionine-γ-lyase (CGL). In certain aspects, there may be a polypeptide comprising a modified human CGL capable of degrading methionine. In some embodiments, the polypeptide may be capable of degrading methionine under physiological conditions. For example, the polypeptide may have a catalytic efficiency for methionine ($k_{cat}/K_M$) of at least or about 0.01, 0.05, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$ $M^{-1}s^{-1}$ or any range derivable therein. In further aspects, the polypeptide may display a catalytic activity towards L-homocystine up to $k_{cat}/K_M$ of 100, 95, 90, 85, 80, 75, 70, 65, 60, 55, 50, 45, 40, 35, 30, 25, 20, 15, 10, 9, 8, 7, 6, 5, 4, 3, 2, 1, 0.9, 0.8, 0.7, 0.6, 0.5, 0.4, 0.3, 0.2, 0.1, 0.05, 0.01, 0.005, 0.001 $M^{-1}s^{-1}$ or any range derivable therein.

A modified polypeptide as discussed above may be characterized as having a certain percentage of identity as compared to an unmodified polypeptide (e.g., a native polypeptide) or to any polypeptide sequence disclosed herein. For example, the unmodified polypeptide may comprise at least or up to about 10, 20, 30, 40, 50, 60, 70, 80, 90, 100, 150, 200, 250, 300, 350, 400 residues (or any range derivable therein) of a native primate cystathionase (i.e., cystathionine-γ-lyase). The percentage identity may be about, at most or at least 50%, 55%, 60%, 65%, 70%, 75%, 80%, 85%, 90%, 95%, 96%, 97%, 98%, 99% or 100% (or any range derivable therein) between the unmodified portions of a modified polypeptide (i.e., the sequence of the modified polypeptide excluding any substitutions at amino acid positions 59, 63, 91, 119, 268, 311, 339 and/or 353) and the native polypeptide. It is also contemplated that the percent identity discussed above may relate to a particular modified region of a polypeptide as compared to an unmodified region of a polypeptide. For instance, a polypeptide may contain a modified or mutant substrate recognition site of cystathionase that can be characterized based on the identity of the amino acid sequence of the modified or mutant substrate recognition site of cystathionase to that of an unmodified or mutant cystathionase from the same species or across the species. A modified or mutant human polypeptide characterized, for example, as having at least 90% identity to an unmodified cystathionase means that at least 90% of the amino acids in that modified or mutant human polypeptide are identical to the amino acids in the unmodified polypeptide.

Such an unmodified polypeptide may be a native cystathionase, particularly a human isoform or other primate isoforms. For example, the native human cystathionase may have the sequence of SEQ ID NO: 1. Non-limiting examples of other native primate cystathionases include *Pongo abelii* cystathionase (Genbank ID: NP_001124635.1; SEQ ID NO: 7), *Macaca fascicularis* cystathionase (Genbank ID: AAW71993.1; SEQ ID NO: 8), *Pan troglodytes* cystathionase (Genbank ID: XP_513486.2; SEQ ID NO: 9), and *Pan paniscus* cystathionase (Genbank ID: XP_003830652.1; SEQ ID NO: 10). Exemplary native polypeptides include a sequence having about, at most or at least 50%, 55%, 60%, 65%, 70%, 75%, 80%, 85%, 90%, 95%, 96%, 97%, 98%, 99% or 100% identity (or any range derivable therein) of SEQ ID NOs: 1 or 7-10 or a fragment thereof. For example, the native polypeptide may comprise at least or up to about 10, 20, 30, 40, 50, 60, 70, 80, 90, 100, 150, 200, 250, 300, 350, 400, 415 residues (or any range derivable therein) of the sequence of SEQ ID NOs: 1 or 7-10.

In some embodiments, the native CGL may be modified by one or more other modifications, such as chemical modifications, substitutions, insertions, deletions, and/or truncations. For example, the modifications may be at a substrate recognitions site of the native enzyme. In a particular embodiment, the native CGL may be modified by substitutions. For example, the number of substitutions may be four, five, six, seven, or more. In further embodiments, the native CGL may be modified in the substrate recognition site or any location that may affect substrate specificity. For example, the modified polypeptide may have the at least one amino acid substitution at amino acid positions corresponding to E59, S63, L91, R119, K268, T311, E339, and/or 1353 of SEQ ID NO: 1 or amino acid positions of 59, 63, 91, 119, 268, 311, 339, and/or 353 of a primate CGL. For example, the primate may be human, *Pongo abelii, Macaca fascicularis, Pan troglodyte*, or *Pan paniscus*.

In certain embodiments, the substitutions at amino acid positions 59, 63, 91, 119, 268, 311, 339, and/or 353 is an aspartic acid (N), a valine (V), a leucine (L), a methionine (M), an arginine (R), a glycine (G), an alanine (A), or a serine (S). In particular embodiments, the modification are one or more substitutions selected from the group consisting of E59N, E59I, S63L, L91M, R119L, R119A, K268R, T311G, E339V, and I353S. In a further embodiment, the substitutions may comprise a S63L, L91M, K268R, T311G, E339V, and I353S substitutions. In a still further embodiment, the substitutions may comprise additional substitutions of either E59N or E59I and either R119L or R119A.

In some embodiments, the native CGL may be a human CGL. In a particular embodiment, the substitutions are a combination of E59N, S63L, L91M, R119L, K268R, T311G, I353S, and E339V of human CGL (for example, the modified polypeptide having the amino acid sequence of SEQ ID NO: 3, a fragment or homolog thereof), a combination of E59I, S63L, L91M, R119L, K268R, T311G, I353S, E339V of human CGL (for example, the modified polypeptide having the amino acid sequence of SEQ ID NO: 4, a fragment or homolog thereof), a combination of E59N, S63L, L91M, R119A, K268R, T311G, I353S, and E339V of human CGL (for example, the modified polypeptide having the amino acid sequence of SEQ ID NO: 5, a fragment or homolog thereof), or a combination of E59I, S63L, L91M, R119A, K268R, T311G, I353S, and E339V of human CGL (for example, the modified polypeptide having the amino acid sequence of SEQ ID NO: 6, a fragment or homolog thereof). In a further embodiment, the modified polypeptide may be a *Pongo abelii* CGL-NLMLRGSV mutant (SEQ ID NO: 11), *Pongo abelii* CGL-ILMLRGSV mutant (SEQ ID NO: 12), *Pongo abelii* CGL-NLMARGSV mutant (SEQ ID NO: 13), *Pongo abelii* CGL-ILMARGSV mutant (SEQ ID NO: 14), *Macaca fascicularis* CGL-NLMLRGSV mutant (SEQ ID NO: 15), *Macaca fascicularis* CGL-ILMLRGSV mutant (SEQ ID NO: 16), *Macaca fascicularis* CGL-NLMARGSV mutant (SEQ ID NO: 17), *Macaca fascicularis* CGL-ILMARGSV mutant (SEQ ID NO: 18), *Pan troglodytes* CGL-NLMLRGSV mutant (SEQ ID NO: 19), *Pan troglodytes* CGL-ILMLRGSV mutant (SEQ ID NO: 20), *Pan troglodytes* CGL-NLMARGSV mutant (SEQ ID NO: 21), *Pan troglodytes* CGL-ILMARGSV mutant (SEQ ID NO: 22), *Pan paniscus* CGL-NLMLRGSV mutant (SEQ ID NO: 23), *Pan paniscus* CGL-ILMLRGSV mutant (SEQ ID NO: 24), *Pan paniscus* CGL-NLMARGSV mutant (SEQ ID NO: 25), or *Pan paniscus* CGL-ILMARGSV mutant (SEQ ID NO: 26).

In some aspects, the present invention also contemplates polypeptides comprising the modified CGL linked to a heterologous amino acid sequence. For example, the modified CGL may be linked to the heterologous amino acid sequence as a fusion protein. In a particular embodiment, the modified CGL may be linked to amino acid sequences, such as an IgG Fc, albumin, an albumin binding peptide, or an XTEN polypeptide for increasing the in vivo half-life.

To increase serum stability, the modified CGL may be linked to one or more polyether molecules. In a particular embodiment, the polyether may be polyethylene glycol (PEG). The modified polypeptide may be linked to PEG via specific amino acid residues, such as lysine or cysteine. For therapeutic administration, such a polypeptide comprising the modified CGL may be dispersed in a pharmaceutically acceptable carrier.

In some aspects, a nucleic acid encoding such a modified CGL is contemplated. In some embodiments, the nucleic acid has been codon optimized for expression in bacteria. In particular embodiments, the bacteria is *E. coli*. In other aspects, the nucleic acid has been codon optimized for expression in fungus (e.g., yeast), insects, or mammals. The present invention further contemplates vectors, such as expression vectors, containing such nucleic acids. In particular embodiments, the nucleic acid encoding the modified CGL is operably linked to a promoter, including but not limited to heterologous promoters. In one embodiment, a modified CGL may be delivered to a target cell by a vector (e.g., a gene therapy vector). Such viruses may have been modified by recombinant DNA technology to enable the expression of the modified CGL-encoding nucleic acid in the target cell. These vectors may be derived from vectors of non-viral (e.g., plasmids) or viral (e.g., adenovirus, adenoassociated virus, retrovirus, lentivirus, herpes virus, or vaccinia virus) origin. Non-viral vectors are preferably complexed with agents to facilitate the entry of the DNA across the cellular membrane. Examples of such non-viral vector complexes include the formulation with polycationic agents, which facilitate the condensation of the DNA and lipid-based delivery systems. An example of a lipid-based delivery system would include liposome based delivery of nucleic acids.

In still further aspects, the present invention further contemplates host cells comprising such vectors. The host cells may be bacteria (e.g., *E. coli*), fungal cells (e.g., yeast), insect cells, or mammalian cells. To further differentiate desired CGL mutants with methionine degrading activity from the native CGL, host cells having deletions of ilvA and metA (e.g., *E. coli* $ilvA^{-}metA^{-}$) may be prepared and used to identify desired mutants.

In some embodiments, the vectors are introduced into host cells for expressing the modified CGL. The proteins may be expressed in any suitable manner. In one embodiment, the proteins are expressed in a host cell such that the protein is glycosylated. In another embodiment, the proteins are expressed in a host cell such that the protein is aglycosylated.

Certain aspects of the present invention also contemplate methods of treatment by the administration of the modified CGL peptide, the nucleic acid encoding the modified CGL in a gene therapy vector, or the formulation of the present invention, and in particular methods of treating tumor cells or subjects with cancer. The subject may be any animal, such as a mouse. For example, the subject may be a mammal, particularly a primate, and more particularly a human patient. In some embodiments, the method may comprise selecting a patient with cancer. In certain aspects, the subject or patient may be maintained on a methionine-restricted diet or a normal diet.

In some embodiments, the cancer is any cancer that is sensitive to methionine depletion. In one embodiment, the present invention contemplates a method of treating a tumor cell or a cancer patient comprising administering a formulation comprising such a polypeptide. In some embodiments, the administration occurs under conditions such that at least a portion of the cells of the cancer are killed. In another embodiment, the formulation comprises such a modified CGL with methionine degrading activity at physiological conditions and further comprising an attached polyethylene glycol chain. In some embodiment, the formulation is a pharmaceutical formulation comprising any of the above discussed CGL variants and pharmaceutically acceptable excipients. Such pharmaceutically acceptable excipients are well known to those of skill in the art. All of the above CGL variants may be contemplated as useful for human therapy.

In a further embodiment, there may also be provided a method of treating a tumor cell comprising administering a formulation comprising a non-bacterial (mammalian, e.g., primate or mouse) modified CGL that has methionine degrading activity or a nucleic acid encoding thereof.

Because tumor cells are dependent upon their nutrient medium for methionine, the administration or treatment may be directed to the nutrient source for the cells, and not necessarily the cells themselves. Therefore, in an in vivo application, treating a tumor cell includes contacting the nutrient medium for a population of tumor cells with the engineered methioninase. In this embodiment, the medium can be blood, lymphatic fluid, spinal fluid and the like bodily fluid where methionine depletion is desired.

In accordance with certain aspects of the present invention, such a formulation containing the engineered methioninase can be administered intravenously, intradermally, intraarterially, intraperitoneally, intralesionally, intracranially, intraarticularly, intraprostaticaly, intrapleurally, intrasynovially, intratracheally, intranasally, intravitreally, intravaginally, intrarectally, intratumorally, intramuscularly, subcutaneously, subconjunctival, intravesicularlly, mucosally, intrapericardially, intraumbilically, intraocularly, orally, topically, by inhalation, infusion, continuous infusion, localized perfusion, via a catheter, via a lavage, in lipid compositions (e.g., liposomes), or by other method or any combination of the forgoing as would be known to one of ordinary skill in the art.

In a further embodiment, the method may also comprise administering at least a second anticancer therapy to the subject. The second anticancer therapy may be a surgical therapy, chemotherapy, radiation therapy, cryotherapy, hormone therapy, immunotherapy or cytokine therapy.

In one embodiment, a composition comprising an engineered methioninase or a nucleic acid encoding an engineered methioninase is provided for use in the treatment of a tumor in a subject. In another embodiment, the use of an engineered methioninase or a nucleic acid encoding an engineered methioninase in the manufacture of a medicament for the treatment of a tumor is provided. Said engineered methioninase may be any engineered methioninase of the embodiments.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding," with reference to a nucleic acid, are used to make the invention readily understandable by the skilled artisan; however, these terms may be used interchangeably with "comprise" or "comprising," respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
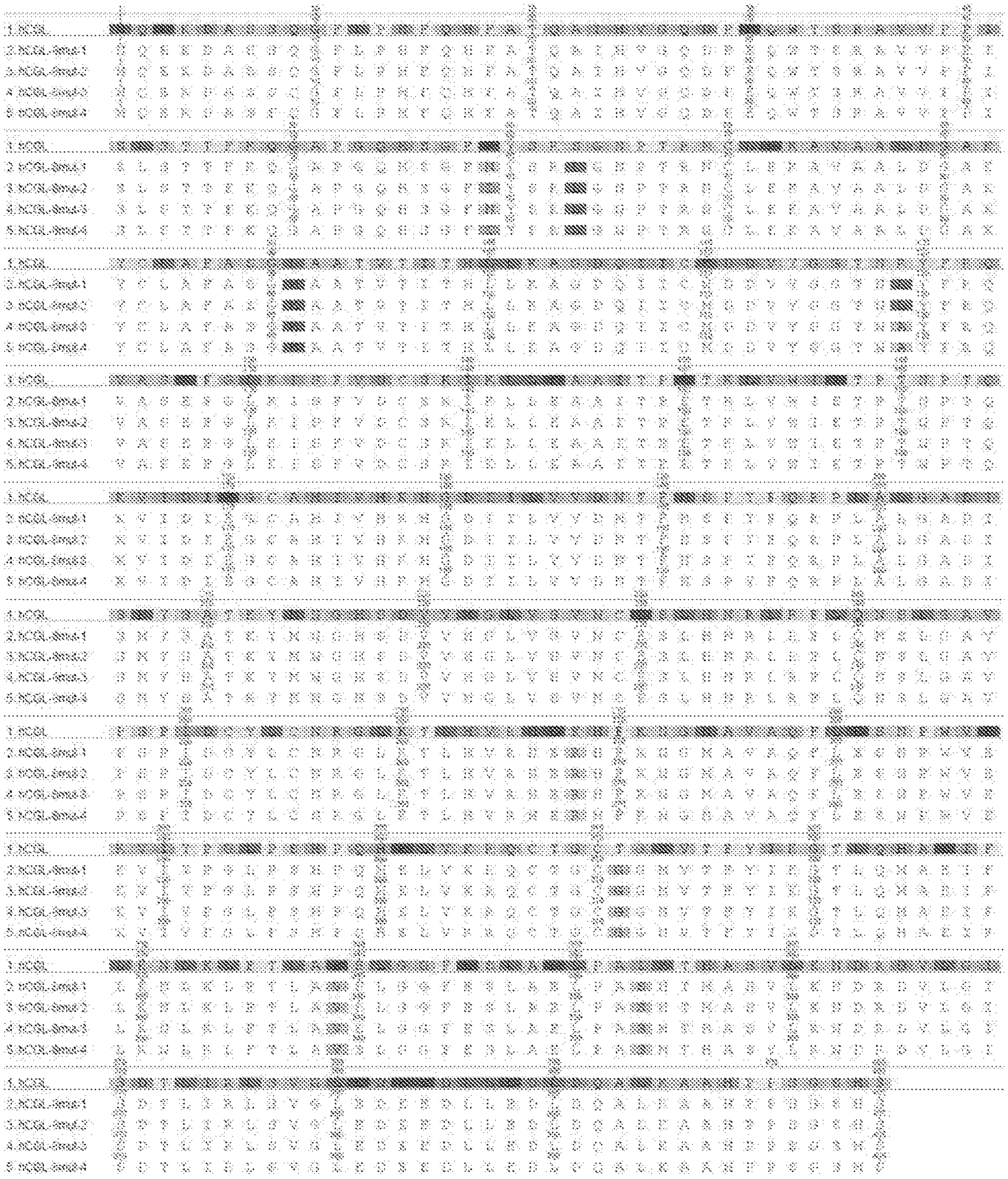
FIG. 1—Sequence alignment of hCGL with hCGL-8mut-1-4. Highlighted residues indicate mutated residues and their position. hCGL=SEQ ID NO: 1; hCGL-8mut-1=SEQ ID NO: 3; hCGL-8mut-2=SEQ ID NO: 4; hCGL-8mut-3=SEQ ID NO: 5; and hCGL-8mut-4=SEQ ID NO: 6.

The present invention discloses compositions of matter for improved human methionine-γ-lyase (hMGL) relative to the hMGL-NLV mutant (E59N, R119L, E339V). These mutants display higher catalytic activity and thus lower concentrations of therapeutic agent may be required for dosing of patients. These engineered human enzymes degrade the amino acid L-methionine.

These compositions provide a way to specifically target tumor cells through a cancer-specific metabolic defect. While bacterial enzymes can also perform the chemistry, their use has proven highly unstable and immunogenic.

I. DEFINITIONS

As used herein the terms “protein” and “polypeptide” refer to compounds comprising amino acids joined via peptide bonds and are used interchangeably.

As used herein, the term “fusion protein” refers to a chimeric protein containing proteins or protein fragments operably linked in a non-native way.

As used herein, the term “half-life” (½-life) refers to the time that would be required for the concentration of a polypeptide thereof to fall by half in vitro or in vivo, for example, after injection in a mammal.

The terms “in operable combination,” “in operable order,” and “operably linked” refer to a linkage wherein the components so described are in a relationship permitting them to function in their intended manner, for example, a linkage of nucleic acid sequences in such a manner that a nucleic acid molecule capable of directing the transcription of a given gene and/or the synthesis of desired protein molecule, or a linkage of amino acid sequences in such a manner so that a fusion protein is produced.

The term “linker” is meant to refer to a compound or moiety that acts as a molecular bridge to operably link two different molecules, wherein one portion of the linker is operably linked to a first molecule, and wherein another portion of the linker is operably linked to a second molecule.

The term “PEGylated” refers to conjugation with polyethylene glycol (PEG), which has been widely used as a drug carrier, given its high degree of biocompatibility and ease of modification. PEG can be coupled (e.g., covalently linked) to active agents through the hydroxy groups at the end of the PEG chain via chemical methods; however, PEG itself is limited to at most two active agents per molecule. In a different approach, copolymers of PEG and amino acids have been explored as novel biomaterial that would retain the biocompatibility of PEG, but that would have the added advantage of numerous attachment points per molecule (thus providing greater drug loading), and that can be synthetically designed to suit a variety of applications.

The term “gene” refers to a DNA sequence that comprises control and coding sequences necessary for the production of a polypeptide or precursor thereof. The polypeptide can be encoded by a full-length coding sequence or by any portion of the coding sequence so as the desired enzymatic activity is retained.

The term “native” refers to the typical form of a gene, a gene product, or a characteristic of that gene or gene product when isolated from a naturally occurring source. A native form is that which is most frequently observed in a natural population and is thus arbitrarily designated the normal or wild-type form. In contrast, the term “modified,” “variant,” or “mutant” refers to a gene or gene product that displays modification in sequence and functional properties (i.e., altered characteristics) when compared to the native gene or gene product.

The term “vector” is used to refer to a carrier nucleic acid molecule into which a nucleic acid sequence can be inserted for introduction into a cell where it can be replicated. A nucleic acid sequence can be “exogenous,” which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term “expression vector” refers to any type of genetic construct comprising a nucleic acid coding for an RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of “control sequences,” which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

The term “therapeutic benefit” or “therapeutically effective” as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

The term "$K_M$" as used herein refers to the Michaelis-Menten constant for an enzyme and is defined as the concentration of the specific substrate at which a given enzyme yields one-half its maximum velocity in an enzyme catalyzed reaction. The term "$k_{cat}$" as used herein refers to the turnover number or the number of substrate molecules each enzyme site converts to product per unit time, and in which the enzyme is working at maximum efficiency. The term "$k_{cat}/K_M$" as used herein is the specificity constant, which is a measure of how efficiently an enzyme converts a substrate into product.

The term "cystathionine-γ-lyase" (CGL or cystathionase) refers to any enzyme that catalyzes the hydrolysis of cystathionine to cysteine. For example, it includes primate forms of cystathionine-γ-lyase, or particularly, human forms of cystathionine-γ-lyase.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of a methioninase.

"Subject" and "patient" refer to either a human or non-human, such as primates, mammals, and vertebrates. In particular embodiments, the subject is a human.

II. METHIONINE-γ-LYASE AND CYSTATHIONINE-γ-LYASE

A lyase is an enzyme that catalyzes the breaking of various chemical bonds, often forming a new double bond or a new ring structure. For example, an enzyme that catalyzes this reaction would be a lyase: ATP→cAMP+PPi. Lyases differ from other enzymes in that they only require one substrate for the reaction in one direction, but two substrates for the reverse reaction.

A number of pyrioxal-5'-phosphate (PLP)-dependent enzymes are involved in the metabolism of cysteine, homocysteine, and methionine, and these enzymes form an evolutionarily related family, designated as Cys/Met metabolism PLP-dependent enzymes. These enzymes are proteins of about 400 amino acids and the PLP group is attached to a lysine residue located in the central location of the polypeptide. Members of this family include cystathionine-γ-lyase (CGL), cystathionine-γ-synthase (CGS), cystathionine-3-lyase (CBL), methionine-γ-lyase (MGL), and O-acetylhomoserine (OAH)/O-acetyl-serine (OAS) sulfhydrylase (OSHS). Common to all of them is the formation of a Michaelis complex leading to an external substrate aldimine. The further course of the reaction is determined by the substrate specificity of the particular enzyme.

For example, the inventors introduced specific mutations into a PLP-dependent lyase family member, such as the human cystathionine-γ-lyase, to change its substrate specificity. In this manner the inventors produced novel variants with the de novo ability to degrade L-Met as a substrate with substantially higher catalytic activity than hMGL-NLV. In other embodiments, a modification of other PLP-dependent enzymes for producing novel methionine degrading activity may also be contemplated.

As a PLP-dependent enzyme, a methionine-γ-lyase (EC 4.4.1.11) is an enzyme that catalyzes the chemical reaction: L-methionine+$H_2O$→methanethiol+$NH_3$+2-oxobutanoate. Thus, the two substrates of this enzyme are L-methionine and $H_2O$, whereas its three products are methanethiol, $NH_3$, and 2-oxobutanoate. This enzyme belongs to the family of lyases, specifically the class of carbon-sulfur lyases. The systematic name of this enzyme class is L-methionine methanethiol-lyase (deaminating 2-oxobutanoate-forming). Other names in common use include L-methioninase, methionine lyase, methioninase, methionine dethiomethylase, L-methionine-gamma-lyase, and L-methionine methanethiol-lyase (deaminating). This enzyme participates in selenoamino acid metabolism. It employs one cofactor, pyridoxal-5'-phosphate.

Methioninase usually consists of 389-441 amino acids and forms a homotetramer. Methioninase enzymes are generally composed of four identical subunits of molecular weight of ~45 kDa (Sridhar et al., 2000; Nakamura et al., 1984). The structure of the enzyme was elucidated by crystallization (Kudou et al., 2007). Each segment of the tetramer is composed of three regions: an extended N-terminal domain (residues 1-63) that includes two helices and three beta-strands, a large PLP binding domain (residues 64-262) that is made up of a mostly parallel seven stranded beta-sheet that is sandwiched between eight alpha-helices, and a C-terminal domain (residues 263-398). The cofactor PLP is required for catalytic function. Amino acids important for catalysis have been identified based on the structure. Tyr59 and Arg61 of neighboring subunits, which are also strongly conserved in other c-family enzymes, contact the phosphate group of PLP. These residues are important as the main anchor within the active site. Lys240, Asp241, and Arg61 of one monomer and Tyr114 and Cysl16 of an adjacent monomer form a hydrogen-bond network in the methioninase active site that confers specificity to the enzyme.

Cystathionine-γ-lyase (CGL or cystathionase) is an enzyme that breaks down cystathionine into cysteine and α-ketobutyrate. Pyridoxal phosphate is a prosthetic group of this enzyme. Although mammals do not have a methioninase (MGL), they do have cystathionase with sequence, structural, and chemical homology to the bacterial MGL enzymes. As shown in the Examples, protein engineering was used to convert cystathionase, which has no activity for the degradation of L-Methionine, into an enzyme that can degrade this amino acid at a high rate.

III. METHIONINASE ENGINEERING

Since humans do not produce methionine-γ-lyase (MGL or methioninase) it is necessary to engineer methioninases for human therapy that have high activity and specificity for degrading methionine under physiological conditions, as well as high stability in physiological fluids, such as serum, and are also non-immunogenic because they are native proteins that normally elicit immunological tolerance.

Due to the undesired immunogenic effects seen in animal studies with pMGL (MGL from *P. putida*), it is desirable to engineer L-methionine degradation activity in a human enzyme. Immunological tolerance to human proteins makes it likely that such an enzyme will be non-immunogenic or minimally immunogenic and therefore well tolerated.

Certain aspects of novel enzymes with MGL activity as engineered methioninase address these needs. Although mammals do not have a MGL, they do have a cystathionine-γ-lyase (CGL) that has sequence, structural, and chemical homology to the bacterial MGL enzymes. CGL is a tetramer that catalyzes the last step in the mammalian transsulfuration pathway (Rao et al., 1990). CGL catalyzes the conversion of L-cystathionine to L-cysteine, alpha-ketobutyrate, and ammonia. The human CGL (hCGL) cDNA had previously been cloned and expressed, but with relatively low yields (~5 mg/L culture) (Lu et al., 1992; Steegborn et al., 1999).

For example, there have been provided methods and compositions related to a primate (particularly human) cystathionine-γ-lyase (CGL or cystathionase) modified via mutagenesis to hydrolyze methionine with high efficiency, while the cystathionine-γ-lyase does not exhibit methioninase activity in its native form.

Some embodiments concern modified proteins and polypeptides. Particular embodiments concern a modified protein or polypeptide that exhibits at least one functional activity that is comparable to the unmodified version, preferably, the methioninase enzyme activity. In further aspects, the protein or polypeptide may be further modified to increase serum stability. Thus, when the present application refers to the function or activity of "modified protein" or a "modified polypeptide," one of ordinary skill in the art would understand that this includes, for example, a protein or polypeptide that possesses an additional advantage over the unmodified protein or polypeptide, such as the methioninase enzyme activity. In certain embodiments, the unmodified protein or polypeptide is a native cystathionine-γ-lyase, specifically a human cystathionine-γ-lyase. It is specifically contemplated that embodiments concerning a "modified protein" may be implemented with respect to a "modified polypeptide," and vice versa.

Determination of activity may be achieved using assays familiar to those of skill in the art, particularly with respect to the protein's activity, and may include for comparison purposes, for example, the use of native and/or recombinant versions of either the modified or unmodified protein or polypeptide. For example, the methioninase activity may be determined by any assay to detect the production of any substrates resulting from conversion of methionine, such as alpha-ketobutyrate, methanethiol, and/or ammonia.

In certain embodiments, a modified polypeptide, such as a modified cystathionine-γ-lyase, may be identified based on its increase in methionine degrading activity. For example, substrate recognition sites of the unmodified polypeptide may be identified. This identification may be based on structural analysis or homology analysis. A population of mutants involving modifications of such substrate recognitions sites may be generated. In a further embodiment, mutants with increased methionine degrading activity may be selected from the mutant population. Selection of desired mutants may include methods, such as detection of byproducts or products from methionine degradation.

Modified proteins may possess deletions and/or substitutions of amino acids; thus, a protein with a deletion, a protein with a substitution, and a protein with a deletion and a substitution are modified proteins. In some embodiments, these modified proteins may further include insertions or added amino acids, such as with fusion proteins or proteins with linkers, for example. A "modified deleted protein" lacks one or more residues of the native protein, but may possess the specificity and/or activity of the native protein. A "modified deleted protein" may also have reduced immunogenicity or antigenicity. An example of a modified deleted protein is one that has an amino acid residue deleted from at least one antigenic region, that is, a region of the protein determined to be antigenic in a particular organism, such as the type of organism that may be administered the modified protein.

Substitution or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a control polypeptide are included, provided the biological activity of the protein is maintained. A modified protein may be biologically functionally equivalent to its native counterpart in certain aspects.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

IV. ENZYMATIC L-METHIONINE DEPLETION FOR THERAPY

In certain aspects, the polypeptides may be used for the treatment of diseases, including cancers that are sensitive to methionine depletion, such as hepatocellular carcinoma, melanoma, and renal cell carcinoma, with novel enzymes that deplete L-methionine. The invention specifically discloses treatment methods using modified cystathionine-γ-lyase with methionine degrading activity. As described below, as currently available methionine-γ-lyases are typically bacterially-derived proteins, there remain several problems for their use in human therapy. Certain embodiments of the present invention provide novel enzymes with methionine-γ-lyase activity for increased therapeutic efficacy.

Methionine (L-Met) depletion has long been studied as a potential treatment for cancer. While L-Met is an essential amino acid, many malignant human cell lines and tumors have been shown to have a relatively greater requirement for methionine (Halpern et al., 1974; Kreis and Goodenow, 1978; Breillout et al., 1990; Kreis et al., 1980; Kreis, 1979). Methionine-dependent tumor cell lines present no or low levels of methionine synthase, the enzyme that normally recycles homocysteine back to L-Met (Halpern et al., 1974;

Ashe et al., 1974). Most normal cells can grow on precursors, such as homocysteine and homocystine, whereas many malignant cells must scavenge L-Met directly from their extracellular environment. Also, any rapidly growing neoplasm can be adversely affected by the lack of essential building blocks necessary for growth. Methionine is particularly important as its depletion leads not only to diminished protein synthesis, but also dysregulated S-adenosylmethionine (SAM)-dependent methylation pathways, which are particularly important for gene regulation.

The differences in methionine requirements between normal and cancer cells provide a therapeutic opportunity. Enzymatic methionine depletion has been explored in a number of animal model studies as well as Phase I clinical trials (Tan et al., 1997a; Tan et al., 1996a; Lishko et al., 1993; Tan et al., 1996b; Yoshioka et al., 1998; Yang et al., 2004a; Yang et al., 2004b; Tan et al., 1997b).

Because humans lack a methionine hydrolyzing enzyme, bacterial L-methionine-γ-lyases, MGL, from various sources have been evaluated for cancer therapy. Methionine-γ-lyase catalyzes the conversion of methionine to methanethiol, alpha-ketobutyrate, and ammonia. Bacterial enzymes from various sources have been purified and tested as methionine depleting agents against cancer cell lines. The *P. putida* (pMGL) source was selected for therapeutic applications due to its high catalytic activity, low $K_{M\ value}$, and relatively high $k_{cat}$ value (Esaki and Soda, 1987; Ito et al., 1976), in comparison to other sources. Furthermore, the gene for pMGL has been cloned into *E. coli* and the protein was expressed at a high protein yield (Tan et al., 1997a; Hori et al., 1996).

In vivo studies have been performed on animal models, as well as humans. Tan et al. (1997a) performed studies with human tumors xenografted into nude mice and found that lung, colon, kidney, brain, prostate, and melanoma cancers were all sensitive to pMGL. Additionally, no toxicity was detected at effective doses, as was determined by an absence of weight loss in the animals. Half-life in these experiments was determined to be only 2 h as measured from collected blood samples. Additionally, infusion of PLP is required in order to maintain MGL activity. In spite of the very short half-life, Tan et al. (1997a) reported inhibition of tumor growth in comparison to a saline control.

Yang et al. (2004b) studied the pharmacokinetics, the pharmacodynamics in terms of methionine depletion, the antigenicity, and toxicity of MGL in a primate model. Dose-ranging studies were performed at 1000-4000 units/kg administered intravenously. The highest dose was able to reduce plasma methionine to an undetectable level (less than 0.5 μM) by 30 min after injection, with the methionine level remaining undetectable for 8 h. Pharmacokinetic analysis showed that pMGL was eliminated with a half-life of 2.5 h. An administration of that dose every 8 h/day for 2 weeks resulted in a steady-state depletion of plasma methionine to less than 2 μM. Mild toxicity was observed through decreased food intake and slight weight loss. Unfortunately, re-challenge on day 28 resulted in anaphylactic shock and death in one animal indicating that pMGL is highly immunogenic, which is a significant disadvantage for human therapy. Subsequent pretreatment with hydrocortisone prevented the anaphylactic reaction, although vomiting was frequently observed. Additional re-challenges were carried out at days 66, 86, and 116. Anti-rMGL antibodies were detected after the first challenge, and increased in concentration for the duration of treatment.

In response to these observed obstacles to therapeutic implementation of MGL, Yang et al. (2004b) studied the PEGylation of the enzyme and its effect on half-life and immunogenicity. The enzyme was coupled to methoxypolyethylene glycol succinimidyl glutarate (MEGC-PEG-5000). Dose ranging studies were again performed and 4000 units/kg (90 mg/kg) was sufficient to reduce plasma methionine to <5 μmol/L for 12 h. Pharmacokinetic analysis showed a 36-fold improvement in the serum clearance half-life of the PEGylated enzyme, as compared to the unPEGylated enzyme. PEGylating also attenuated immunogenicity somewhat as only slight toxicities of decreased food intake and minor weight loss were observed. However, the activity half-life was not improved as L-Met levels were only kept below detection levels for 12 h as opposed to 8 h for the unPEGylated enzyme. These results, though promising for the use of an L-Met depleting enzyme as an anti-neoplastic agent, are challenged by significant shortcomings of immunogenicity and pharmacokinetics.

Certain aspects of the present invention provide a modified cystathionine-γ-lyase with methionine degrading activity for treating diseases, such as tumors. Particularly, the modified polypeptide may have human polypeptide sequences and thus may prevent allergic reactions in human patients, allow repeated dosing, and increase the therapeutic efficacy.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma;

adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The engineered human methioninase derived from cystathionase may be used herein as an antitumor agent in a variety of modalities for depleting methionine from a tumor cell, tumor tissue, or the circulation of a mammal with cancer, or for depletion of methionine where its depletion is considered desirable.

Depletion can be conducted in vivo in the circulation of a mammal, in vitro in cases where methionine depletion in tissue culture or other biological mediums is desired, and in ex vivo procedures where biological fluids, cells, or tissues are manipulated outside the body and subsequently returned to the body of the patient mammal. Depletion of methionine from circulation, culture media, biological fluids, or cells is conducted to reduce the amount of methionine accessible to the material being treated, and therefore comprises contacting the material to be depleted with a methionine-depleting amount of the engineered human methioninase under methionine-depleting conditions as to degrade the ambient methionine in the material being contacted.

Because tumor cells are dependent upon their nutrient medium for methionine, the depletion may be directed to the nutrient source for the cells, and not necessarily the cells themselves. Therefore, in an in vivo application, treating a tumor cell includes contacting the nutrient medium for a population of tumor cells with the engineered methioninase. In this embodiment, the medium may be blood, lymphatic fluid, spinal fluid and the like bodily fluid where methionine depletion is desired.

A methionine-depleting efficiency can vary widely depending upon the application, and typically depends upon the amount of methionine present in the material, the desired rate of depletion, and the tolerance of the material for exposure to methioninase. Methionine levels in a material, and therefore rates of methionine depletion from the material, can readily be monitored by a variety of chemical and biochemical methods well known in the art. Exemplary methionine-depleting amounts are described further herein, and can range from 0.001 to 100 units (U) of engineered methioninase, preferably about 0.01 to 10 U, and more preferably about 0.1 to 5 U engineered methioninase per milliliter (mL) of material to be treated.

Methionine-depleting conditions are buffer and temperature conditions compatible with the biological activity of a methioninase enzyme, and include moderate temperature, salt, and pH conditions compatible with the enzyme, for example, physiological conditions. Exemplary conditions include about 4-40° C., ionic strength equivalent to about 0.05 to 0.2 M NaCl, and a pH of about 5 to 9, while physiological conditions are included.

In a particular embodiment, the invention contemplates methods of using engineered methioninase as an antitumor agent, and therefore comprises contacting a population of tumor cells with a therapeutically effective amount of engineered methioninase for a time period sufficient to inhibit tumor cell growth.

In one embodiment, the contacting in vivo is accomplished by administering, by intravenous or intraperitoneal injection, a therapeutically effective amount of a physiologically tolerable composition comprising an engineered methioninase of this invention to a patient, thereby depleting the circulating methionine source of the tumor cells present in the patient. The contacting of engineered methioninase can also be accomplished by administering the engineered methioninase into the tissue containing the tumor cells.

A therapeutically effective amount of an engineered methioninase is a predetermined amount calculated to achieve the desired effect, i.e., to deplete methionine in the tumor tissue or in a patient's circulation, and thereby cause the tumor cells to stop dividing. Thus, the dosage ranges for the administration of engineered methioninase of the invention are those large enough to produce the desired effect in which the symptoms of tumor cell division and cell cycling are reduced. The dosage should not be so large as to cause adverse side effects, such as hyperviscosity syndromes, pulmonary edema, congestive heart failure, and the like. Generally, the dosage will vary with age of, condition of, sex of, and extent of the disease in the patient and can be determined by one of skill in the art. The dosage can be adjusted by the individual physician in the event of any complication.

For example, a therapeutically effective amount of an engineered methioninase may be an amount such that when administered in a physiologically tolerable composition is sufficient to achieve an intravascular (plasma) or local concentration of from about 0.001 to about 100 units (U) per mL, preferably above about 0.1 U, and more preferably above 1 U engineered methioninase per mL. Typical dosages can be administered based on body weight, and are in the range of about 5-1000 U/kilogram (kg)/day, preferably about 5-100 U/kg/day, more preferably about 10-50 U/kg/day, and more preferably about 20-40 U/kg/day.

The engineered methioninase can be administered parenterally by injection or by gradual infusion over time. The engineered methioninase can be administered intravenously, intraperitoneally, orally, intramuscularly, subcutaneously, intracavity, transdermally, dermally, can be delivered by peristaltic means, can be injected directly into the tissue containing the tumor cells, or can be administered by a pump connected to a catheter that may contain a potential biosensor or methionine.

The therapeutic compositions containing engineered methioninase are conventionally administered intravenously, as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also contemplated and are typified by an initial administration followed by repeated doses at one or more hour intervals by a subsequent injection or other administration. Exemplary multiple administrations are described herein and are particularly preferred to maintain continuously high serum and tissue levels of engineered methioninase and conversely low serum and tissue levels of methionine. Alternatively, continuous intravenous infusion sufficient to maintain concentrations in the blood in the ranges specified for in vivo therapies are contemplated.

V. CONJUGATES

Compositions and methods of the present invention involve further modification of the engineered methioninase for improvement, such as by forming conjugates with heterologous peptide segments or polymers, such as polyethylene glycol. In further aspects, the engineered methioninase may be linked to PEG to increase the hydrodynamic radius of the enzyme and hence increase the serum persistence. In certain aspects, the disclosed polypeptide may be conjugated to any targeting agent, such as a ligand having the ability to specifically and stably bind to an external receptor or binding site on a tumor cell (U.S. Patent Publ. 2009/0304666).

A. Fusion Proteins

Certain embodiments of the present invention concern fusion proteins. These molecules may have the engineered human methioninase linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

In a particular embodiment, the engineered human methioninase may be linked to a peptide that increases the in vivo half-life, such as an XTEN polypeptide (Schellenberger et al., 2009), IgG Fc domain, albumin, or an albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

B. Linkers

In certain embodiments, the engineered methioninase may be chemically conjugated using bifunctional cross-linking reagents or fused at the protein level with peptide linkers.

Bifunctional cross-linking reagents have been extensively used for a variety of purposes, including preparation of affinity matrices, modification and stabilization of diverse structures, identification of ligand and receptor binding sites, and structural studies. Suitable peptide linkers may also be used to link the engineered methioninase, such as Gly-Ser linkers.

Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidine-, indole-, carboxyl-specific groups. Of these, reagents directed to free amino groups have become especially popular because of their commercial availability, ease of synthesis, and the mild reaction conditions under which they can be applied.

A majority of heterobifunctional cross-linking reagents contain a primary amine-reactive group and a thiol-reactive group. In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling, in one example, of aldehydes to free thiols. The cross-linking reagent can be modified to cross-link various functional groups.

Additionally, any other linking/coupling agents and/or mechanisms known to those of skill in the art may be used to combine human engineered methioninase, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo. These linkers are thus one group of linking agents.

In addition to hindered cross-linkers, non-hindered linkers also can be employed in accordance herewith. Other useful cross-linkers, not considered to contain or generate a protected disulfide, include SATA, SPDP, and 2-iminothiolane (Wawrzynczak and Thorpe, 1987). The use of such cross-linkers is well understood in the art. Another embodiment involves the use of flexible linkers.

Once chemically conjugated, the peptide generally will be purified to separate the conjugate from unconjugated agents and from other contaminants. A large number of purification techniques are available for use in providing conjugates of a sufficient degree of purity to render them clinically useful.

Purification methods based upon size separation, such as gel filtration, gel permeation, or high performance liquid chromatography, will generally be of most use. Other chromatographic techniques, such as Blue-Sepharose separation, may also be used. Conventional methods to purify the fusion proteins from inclusion bodies may be useful, such as using weak detergents, such as sodium N-lauroyl-sarcosine (SLS).

C. PEGylation

In certain aspects of the invention, methods and compositions related to PEGylation of engineered methioninase are disclosed. For example, the engineered methioninase may be PEGylated in accordance with the methods disclosed herein.

PEGylation is the process of covalent attachment of poly(ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity) or increase the hydrodynamic size (size in solution) of the agent, which prolongs its circulatory time by reducing renal clearance. PEGylation can also provide water solubility to hydrophobic drugs and proteins.

The first step of the PEGylation is the suitable functionalization of the PEG polymer at one or both terminals. PEGs that are activated at each terminus with the same reactive moiety are known as "homobifunctional," whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates, and carbonates. In the second generation PEGylation chemistry more efficient functional groups, such as aldehyde, esters, amides, etc., are made available for conjugation.

As applications of PEGylation have become more and more advanced and sophisticated, there has been an increase in need for heterobifunctional PEGs for conjugation. These heterobifunctional PEGs are very useful in linking two entities, where a hydrophilic, flexible, and biocompatible spacer is needed. Preferred end groups for heterobifunctional PEGs are maleimide, vinyl sulfones, pyridyl disulfide, amine, carboxylic acids, and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homo-dimeric PEG-linked molecule.

Proteins are generally PEGylated at nucleophilic sites, such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The thioether formed with the maleimides can be somewhat unstable under alkaline conditions so there may be some limitation to formulation options with this linker. The carbamothioate linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific PEGylation at native cysteinyl residues is seldom carried out, since these residues are usually in the form of disulfide bonds or are required for biological activity. On the other hand, site-directed mutagenesis can be used to incorporate cysteinyl PEGylation sites for thiol-specific linkers. The cysteine mutation must be designed such that it is accessible to the PEGylation reagent and is still biologically active after PEGylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the PEGylation reaction difficult to control on a large scale. PEG aldehyde forms an imine with the amino group, which is then reduced to a secondary amine with sodium cyanoborohydride. Unlike sodium borohydride, sodium cyanoborohydride will not reduce disulfide bonds. However, this chemical is highly toxic and must be handled cautiously, particularly at lower pH where it becomes volatile.

Due to the multiple lysine residues on most proteins, site-specific PEGylation can be a challenge. Fortunately, because these reagents react with unprotonated amino groups, it is possible to direct the PEGylation to lower-pK amino groups by performing the reaction at a lower pH. Generally the pK of the alpha-amino group is 1-2 pH units lower than the epsilon-amino group of lysine residues. By PEGylating the molecule at pH 7 or below, high selectivity for the N-terminus frequently can be attained. However, this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

There are several parameters to consider when developing a PEGylation procedure. Fortunately, there are usually no more than four or five key parameters. The "design of experiments" approach to optimization of PEGylation conditions can be very useful. For thiol-specific PEGylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the PEGylation reaction. For example, if the PEGylation agent is only 70% active, the amount of PEG used should ensure that only active PEG molecules are counted in the protein-to-PEG reaction stoichiometry.

VI. PROTEINS AND PEPTIDES

In certain embodiments, the present invention concerns novel compositions comprising at least one protein or peptide, such as an engineered methioninase. These peptides may be comprised in a fusion protein or conjugated to an agent as described supra.

As used herein, a protein or peptide generally refers, but is not limited to, a protein of greater than about 200 amino acids, up to a full-length sequence translated from a gene; a polypeptide of greater than about 100 amino acids; and/or a peptide of from about 3 to about 100 amino acids. For convenience, the terms "protein," "polypeptide," and "peptide" are used interchangeably herein.

As used herein, an "amino acid residue" refers to any naturally occurring amino acid, any amino acid derivative, or any amino acid mimic known in the art. In certain embodiments, the residues of the protein or peptide are sequential, without any non-amino acids interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid.

Proteins or peptides may be made by any technique known to those of skill in the art, including the expression of proteins, polypeptides, or peptides through standard molecular biological techniques, the isolation of proteins or peptides from natural sources, or the chemical synthesis of proteins or peptides. The nucleotide and protein, polypeptide, and peptide sequences corresponding to various genes have been previously disclosed, and may be found at computerized databases known to those of ordinary skill in the art. One such database is the National Center for Biotechnology Information's Genbank and GenPept databases (available on the world wide web at ncbi.nlm.nih.gov/). The coding regions for known genes may be amplified and/or expressed using the techniques disclosed herein or as would be known to those of ordinary skill in the art. Alternatively, various commercial preparations of proteins, polypeptides, and peptides are known to those of skill in the art.

VII. NUCLEIC ACIDS AND VECTORS

In certain aspects of the invention, nucleic acid sequences encoding an engineered methioninase or a fusion protein containing an engineered human methioninase may be disclosed. Depending on which expression system is used, nucleic acid sequences can be selected based on conventional methods. For example, if the engineered methioninase is derived from human cystathionase and contains multiple codons that are rarely utilized in *E. coli*, then that may interfere with expression. Therefore, the respective genes or variants thereof may be codon optimized for *E. coli* expression. Various vectors may be also used to express the protein of interest, such as engineered methioninase. Exemplary vectors include, but are not limited, plasmid vectors, viral vectors, transposon, or liposome-based vectors.

VIII. HOST CELLS

Host cells may be any that may be transformed to allow the expression and secretion of engineered methioninase and conjugates thereof. The host cells may be bacteria, mammalian cells, yeast, or filamentous fungi. Various bacteria include *Escherichia* and *Bacillus*. Yeasts belonging to the genera *Saccharomyces, Kiuyveromyces, Hansenula*, or *Pichia* would find use as an appropriate host cell. Various species of filamentous fungi may be used as expression hosts, including the following genera: *Aspergillus, Trichoderma, Neurospora, Penicillium, Cephalosporium, Achlya, Podospora, Endothia, Mucor, Cochliobolus*, and *Pyricularia.*

Examples of usable host organisms include bacteria, e.g., *Escherichia coli* MC1061, derivatives of *Bacillus subtilis* BRB1 (Sibakov et al., 1984), *Staphylococcus aureus* SA1123 (Lordanescu, 1975) or *Streptococcus lividans* (Hopwood et al., 1985); yeasts, e.g., *Saccharomyces cerevisiae* AH 22 (Mellor et al., 1983) or *Schizosaccharomyces pombe*; and filamentous fungi, e.g., *Aspergillus nidulans, Aspergillus awamori* (Ward, 1989), or *Trichoderma reesei* (Penttila et al., 1987; Harkki et al., 1989).

Examples of mammalian host cells include Chinese hamster ovary cells (CHO-K1; ATCC CCL61), rat pituitary cells (GH1; ATCC CCL82), HeLa S3 cells (ATCC CCL2.2), rat hepatoma cells (H-4-II-E; ATCCCRL 1548), SV40-transformed monkey kidney cells (COS-1; ATCC CRL 1650), and murine embryonic cells (NIH-3T3; ATCC CRL 1658). The foregoing is meant to be illustrative but not limitative of the many possible host organisms known in the art. In principle, all hosts capable of secretion can be used whether prokaryotic or eukaryotic.

Mammalian host cells expressing the engineered methioninases and/or their fusion proteins are cultured under conditions typically employed to culture the parental cell line. Generally, cells are cultured in a standard medium containing physiological salts and nutrients, such as standard RPMI, MEM, IMEM, or DMEM, typically supplemented with 5%-10% serum, such as fetal bovine serum. Culture conditions are also standard, e.g., cultures are incubated at 37° C. in stationary or roller cultures until desired levels of the proteins are achieved.

IX. PROTEIN PURIFICATION

Protein purification techniques are well known to those of skill in the art. These techniques involve, at one level, the homogenization and crude fractionation of the cells, tissue, or organ to polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, gel exclusion chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various techniques suitable for use in protein purification are well known to those of skill in the art. These include, for example, precipitation with ammonium sulfate, PEG, antibodies and the like, or by heat denaturation, followed by centrifugation; chromatography steps, such as ion exchange, gel filtration, reverse phase, hydroxyapatite, and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide will always be provided in its most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

In certain embodiments a protein or peptide may be isolated or purified, for example, an engineered methioninase, a fusion protein containing the engineered methioninase, or an engineered methioninase post PEGylation. For example, a His tag or an affinity epitope may be comprised in such an engineered methioninase to facilitate purification. Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding. It should be possible to elute the substance without destroying the sample or the ligand.

Size exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase.

The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

High-performance liquid chromatography (or high-pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

X. PHARMACEUTICAL COMPOSITIONS

It is contemplated that the novel methioninase can be administered systemically or locally to inhibit tumor cell growth and, most preferably, to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

It is not intended that the present invention be limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects.

Such compositions are typically prepared as liquid solutions or suspensions, for use as injectables. Suitable diluents and excipients are, for example, water, saline, dextrose, glycerol, or the like, and combinations thereof. In addition, if desired, the compositions may contain minor amounts of auxiliary substances, such as wetting or emulsifying agents, stabilizing agents, or pH buffering agents.

Where clinical applications are contemplated, it may be necessary to prepare pharmaceutical compositions comprising proteins, antibodies, and drugs in a form appropriate for the intended application. Generally, pharmaceutical compositions may comprise an effective amount of one or more engineered methioninase or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition that contains at least one engineered methioninase isolated by the method disclosed herein, or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by the FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., 1990, incorporated herein by reference). Except insofar as any conventional carrier is incompatible with the active ingredient, its use in the pharmaceutical compositions is contemplated.

Certain embodiments of the present invention may comprise different types of carriers depending on whether it is to be administered in solid, liquid, or aerosol form, and whether it needs to be sterile for the route of administration, such as injection. The compositions can be administered intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference).

The modified polypeptides may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

Further in accordance with certain aspects of the present invention, the composition suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent, or carrier is detrimental to the recipient or to the therapeutic effectiveness of the composition contained therein, its use in administrable composition for use in practicing the methods is appropriate. Examples of carriers or diluents include fats, oils, water, saline solutions, lipids, liposomes, resins, binders, fillers, and the like, or combinations thereof. The composition may also comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal or combinations thereof.

In accordance with certain aspects of the present invention, the composition is combined with the carrier in any convenient and practical manner, i.e., by solution, suspension, emulsification, admixture, encapsulation, absorption, and the like. Such procedures are routine for those skilled in the art.

In a specific embodiment of the present invention, the composition is combined or mixed thoroughly with a semi-solid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates, such as dextrose, mannose, galactose, fructose, lactose, sucrose, maltose, sorbitol, mannitol, etc.

In further embodiments, the present invention may concern the use of a pharmaceutical lipid vehicle composition that includes an engineered methioninase, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the engineered methioninase or a fusion protein thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above.

XI. COMBINATION TREATMENTS

In certain embodiments, the compositions and methods of the present embodiments involve administration of an engineered methioninase in combination with a second or additional therapy. Such therapy can be applied in the treatment of any disease that is associated with methionine dependency. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an engineered methioninase and a second therapy. A tissue, tumor, or cell can be contacted with one or more compositions or pharmacological formulation(s) comprising one or more of the agents (i.e., an engineered methioninase or an anti-cancer agent), or by contacting the tissue, tumor, and/or cell with two or more distinct compositions or formulations, wherein one composition provides 1) an engineered methioninase, 2) an anti-cancer agent, or 3) both an engineered methioninase and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An engineered methioninase may be administered before, during, after, or in various combinations relative to an anti-cancer treatment. The administrations may be in intervals ranging from concurrently to minutes to days to weeks. In embodiments where the engineered methioninase is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the engineered methioninase and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an engineered methioninase is "A" and an anti-cancer therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine;

vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

XII. KITS

Certain aspects of the present invention may provide kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of an engineered methioninase, optionally formulated as a pharmaceutical, or lyophilized, for use with a delivery device.

Kits may comprise a container with a label. Suitable containers include, for example, bottles, vials, and test tubes. The containers may be formed from a variety of materials, such as glass or plastic. The container may hold a composition that includes an engineered methioninase that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

XIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Cystathionine-γ-Lyase Engineered for Methionine-γ-Lyase Activity

CGL is a tetramer that catalyzes the last step in the mammalian transsulfuration pathway (Rao et al., 1990). CGL catalyzes the conversion of L-cystathionine to L-cysteine, alpha-ketobutyrate, and ammonia. The human CGL (hCGL) cDNA has previously been cloned and expressed, but with relatively low yields (~5 mg/L culture) (Lu et al., 1992; Steegborn et al., 1999). Using sequence and structural alignments of CGL and MGL enzymes as a guide, hCGL was converted to an enzyme for the efficient degradation of methionine.

Example 2

Gene Synthesis and Expression of Improved Modified Human Cystathionine-γ-Lyase The human cystathionine-γ-lyase gene contains multiple codons that are rarely utilized in *E. coli* and can interfere with expression. Thus, in order to optimize protein expression in *E. coli*, the respective genes were assembled with codon optimized oligonucleotides designed using DNA-Works software (Hoover et al., 2002). Each construct contains an N-terminal NcoI restriction site, an in-frame N-terminal $His_6$ tag, and a C-terminal EcoRI site for simplifying cloning. After cloning into a pET28a vector (Novagen), *E. coli* (BL21) containing an appropriate cystathionase expression vector were grown at 37° C. using Terrific Broth (TB) media containing 50 μg/mL kanamycin in shaker flasks at 250 rpm until reaching an $OD_{600}$ of ~0.5-0.6. At this point the cultures were switched to a shaker at 25° C., induced with 0.5 mM IPTG, and allowed to express protein for an additional 12 h. Cell pellets were then collected by centrifugation and re-suspended in an IMAC buffer (10 mM $NaPO_4$/10 mM imidazole/300 mM NaCl, pH 8). After lysis by a French pressure cell, lysates were centrifuged at 20,000×g for 20 min at 4° C., and the resulting supernatant applied to a nickel IMAC column, washed with 10-20 column volumes of IMAC buffer, and then eluted with an IMAC elution buffer (50 mM $NaPO_4$/250 mM imidazole/300 mM NaCl, pH 8). Fractions containing enzyme were then incubated with 10 mM pyridoxal-5'-phosphate (PLP) for an hour at 25° C. Using a 10,000 MWCO centrifugal filter device (AMICON®), proteins were then buffer exchanged several times into a 100 mM PBS, 10% glycerol, pH 7.3 solution. Enzyme aliquots were then flash frozen in liquid nitrogen and stored at −80° C. CGL and CGL variants purified in this manner were >95% homogeneous as assessed by SDS-PAGE and coomassie staining. The yield was calculated to be ~400 mg/L culture based upon the calculated extinction coefficient, $\lambda_{280}$=29,870 $M^{-1}$ $cm^{-1}$ in a final buffer concentration of 6 M guanidinium hydrochloride, 20 mM phosphate buffer, pH 6.5 (Gill and von Hippel, 1989).

Example 3

96-Well Plate Screen for Methionine-γ-Lyase Activity and Ranking Clones

Both MGL and CGL produce 2-ketobutanoic acid from their respective substrates. A colorimetric assay for the detection of α-keto acids using 3-methylbenzothiazolin-2-one hydrazone (MBTH) (Takakura et al., 2004) was scaled to a 96-well plate format for screening small libraries and for ranking clones with the greatest METase (methionine-γ-lyase) activity. This plate screen provides a facile method for picking the most active clones from the mutagenic libraries. Clones displaying greater activity than parental controls are selected for further characterization, thus eliminating the need to purify more than a few variants for kinetic analysis.

Single colonies containing mutagenized hCGL, hCGL or pMGL were picked into 96-well culture plates containing 75 μL of TB media/well containing 50 μg/mL kanamycin. These cultures were then grown at 37° C. on a plate shaker until reaching an $OD_{600}$ of ~0.8-1. After cooling to 25° C., an additional 75 μL of media/well containing 50 μg/mL kanamycin and 0.5 mM IPTG was added. Expression was performed at 25° C. with shaking for 2 h, following which 100 μL of culture/well was transferred to a 96-well assay plate. The assay plates were then centrifuged to pellet the cells, the media was removed, and the cells were lysed by addition of 50 μL/well of B-PER® protein extraction reagent (Pierce). After clearing by centrifugation, the lysate was incubated with 5 mM L-Met at 37° C. for 10-12 h. The reaction was then derivatized by addition of 3 parts of 0.03% MBTH solution in 1 M sodium acetate, pH 5. The plates were heated at 50° C. for 40 min and after cooling were read at 320 nm in a microtiter plate reader.

Example 4

Library Design for Generating Improved Methionine Degrading Variants Derived from hCGL-E59N-R119L-E339V The gene for the hCGL-E59N-R119L-E339V (hCGL-NLV) methionine degrading enzyme was used as a starting point to generate further variants with improvements in activity. Amino acid sequence alignments were generated using MGL and CGL sequences from various organisms. Regions selected for mutagenesis were identified at specific alignment sites where the MGL enzymes all had one conserved residue and the CGL enzymes all had a different conserved residue. Although MGL and CGL have highly homologous structures they do not degrade each other's respective substrate, thus phylogenetically conserved amino acid sequence differences between MGL and CGL enzymes can indicate residues that are important for degrading their respective substrate. Libraries were generated by overlap extension PCR using oligonucleotides containing either a codon for the parent hCGL-NLV template coding for a conserved residue or a codon for the corresponding MGL conserved residue. The final assembled PCR products were digested with NcoI and EcoRI and ligated into pET28a vector with T4 DNA ligase. The resulting ligations were transformed directly into *E. coli* (BL21) and plated on LB-kanamycin plates for subsequent screening as described in Example 3. Two times more colonies than the theoretical diversity of the libraries (i.e., all possible gene sequences encoded by the library) were screened. Clones displaying greater activity than the parent hCGL-NLV variant were isolated and sequenced to identify the mutations conferring improved activity. Clones with improved L-methionine degrading activity were used as templates in iterative rounds of mutagenesis as described.

Example 5

Characterization of Improved Human Methionine Degrading Variants

After several rounds of mutagenesis and screening as described in Examples 3 and 4, five amino acid positions in addition to the original three mutation sites (i.e. E59N-R119L-E339V) were found to confer improved methionine degrading activity compared to hCGL-NLV (SEQ ID NO: 2). These additional positions are located at hCGL (SEQ ID NO: 1) residues 63, 91, 268, 311, and 353 (see, FIG. 1). Mutation of one or more of these positions to S63L, L91M, K268R, T311G, and I353S, in combination with mutations of residues at positions 59, 119, and 339, resulted in improved $k_{cat}/K_M$ values for degrading L-methionine compared to hCGL-NLV. In particular, the variants containing amino acid substitutions corresponding to SEQ ID NO: 3, hCGL-E59N-S63L-L91M-R119L-K268R-T311G-E339V-I353S (hCGL-8mut-1); SEQ ID NO: 4, hCGL-E59I-S63L-L91M-R119L-K268R-T311G-E339V-I353S (hCGL-8mut-2); SEQ ID NO: 5, hCGL-E59N-S63L-L91M-R119A-K268R-T311G-E339V-I353S (hCGL-8mut-3); and SEQ ID NO: 6, hCGL-E59I-S63L-L91M-R119A-K268R-T311G-E339V-I353S (hCGL-8mut-4) were shown to have the highest $k_{cat}/K_M$ values for degrading L-methionine. These variants (hCGL-8mut-(1-4)) were purified to greater than 95% homogeneity as assessed by SDS-PAGE as described in Example 2 and kinetically characterized for their ability to degrade L-Met in a 100 mM PBS buffer at pH 7.3 and 37° C. using a 1 mL scale MBTH assay similar to that described in Example 3.

TABLE 1

Comparison of Michaelis-Menten kinetics of L-methionine degradation at pH 7.3 and 37° C. using hCGL, hCGL-NLV, and improved variants hCGL-8mut(1-4).

| Variant | $k_{cat}\,s^{-1}$ | $K_M$ mM | $k_{cat}/K_M\,s^{-1}M^{-1}$ |
|---|---|---|---|
| hCGL | 0 | 0 | 0 |
| hCGL-NLV | 7.9 | 14 | 560 |
| hCGL-8mut-1 | 7.9 | 2.2 | 3590 |
| hCGL-8mut-2 | 7.1 | 1.4 | 5070 |

TABLE 1-continued

Comparison of Michaelis-Menten kinetics of L-methionine degradation at pH 7.3 and 37° C. using hCGL, hCGL-NLV, and improved variants hCGL-8mut(1-4).

| Variant | $k_{cat}\,s^{-1}$ | $K_M$ mM | $k_{cat}/K_M\,s^{-1}M^{-1}$ |
|---|---|---|---|
| hCGL-8mut-3 | ND | ND | ND |
| hCGL-8mut-4 | 9.8 | 1.8 | 5440 |

ND = not determined

Example 6

Cytotoxicity of hCGL-8Mut-1 Against Tumor Cell Lines

Figure 2:
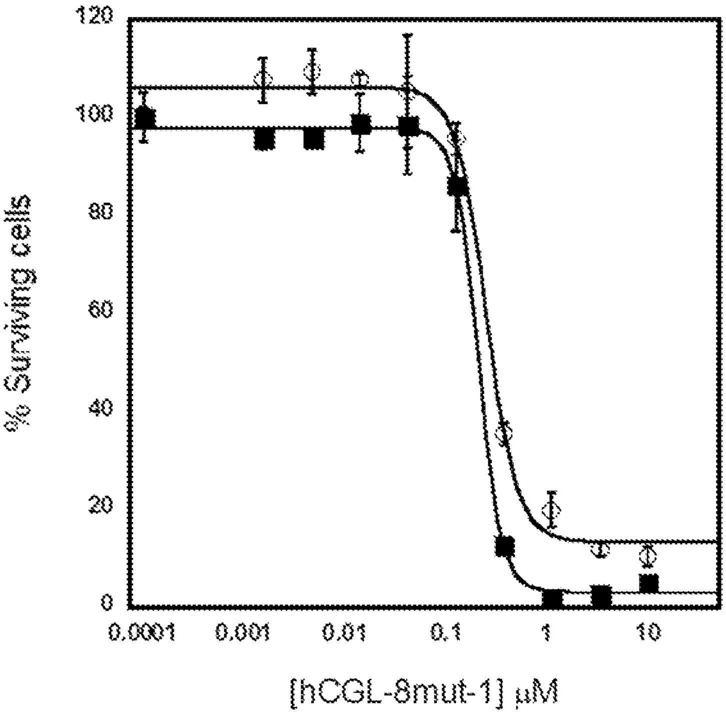
FIG. 2—The effect on prostate tumor cell lines PC3 (open circle) and DU145 (solid square) treated with titrations of hCGL-8mut-1 resulting with apparent $IC_{50}$ values of 0.25 μM and 0.21 μM, respectively.

The in vitro cytotoxicity of hCGL-8mut-1 was assessed against melanoma cell line A375 and prostate cancer cell lines DU145 and PC3. Cells were seeded at ~3000 cells/well in 96-well culture plates in DMEM media for the A375 cells or RPMI-1640 media for the prostate tumor cell lines and allowed to grow for 24 h before treatment with varying concentrations of enzyme. After 5 days of treatment, proliferation was measured using the (3-(4,5-dimethylthiazol-2-yl)-5-(3-carboxymethoxyphenyl)-2-(4-sulfophenyl)-2H-tetrazolium (MTS) assay. Analysis of the resulting data for A375 yielded an apparent $IC_{50}$ value of 0.08 µM and apparent $IC_{50}$ values of 0.21 µM for DU145 and 0.25 µM for PC3 prostate tumor cells (FIG. 2).

Example 7

Pharmacological Preparation of hCGL-8Mut-1

The hCGL-8mut-1 enzyme was purified as described in Example 2 with one exception: after binding to the IMAC column, the protein was washed extensively (90-100 column volumes) with an IMAC buffer containing 0.1% TRITON® 114. Then the column was washed with 10-20 column volumes of IMAC buffer and eluted with an IMAC elution buffer (50 mM $NaPO_4$/250 mM imidazole/300 mM NaCl, pH 8). Washing with TRITON® 114 was employed for endotoxin removal. The purified protein was subjected to buffer exchange into a 100 mM $NaPO_4$ buffer at pH 8.3 using a 10,000 MWCO filtration device (Amicon). Subsequently, PLP was added at a concentration of 10 mM and the protein was incubated for 1 h at 25° C. Methoxy PEG Succinimidyl Carboxymethyl Ester 5000 MW (JenKem Technology) was then added to hCGL-8mut-1 at an 80:1 molar ratio and allowed to react for 1 h at 25° C. under constant stirring. The resulting mixture was extensively buffer exchanged (PBS with 10% glycerol) using a 100,000 MWCO filtration device (Amicon), and sterilized with a 0.2 micron syringe filter (VWR). All PEGylated enzymes were analyzed for lipopolysaccharide (LPS) content using a Limulus Amebocyte Lysate (LAL) kit (Cape Cod Incorporated).

Example 8

Serum Stability of PEGylated hCGL-8Mut-1

Figure 3:
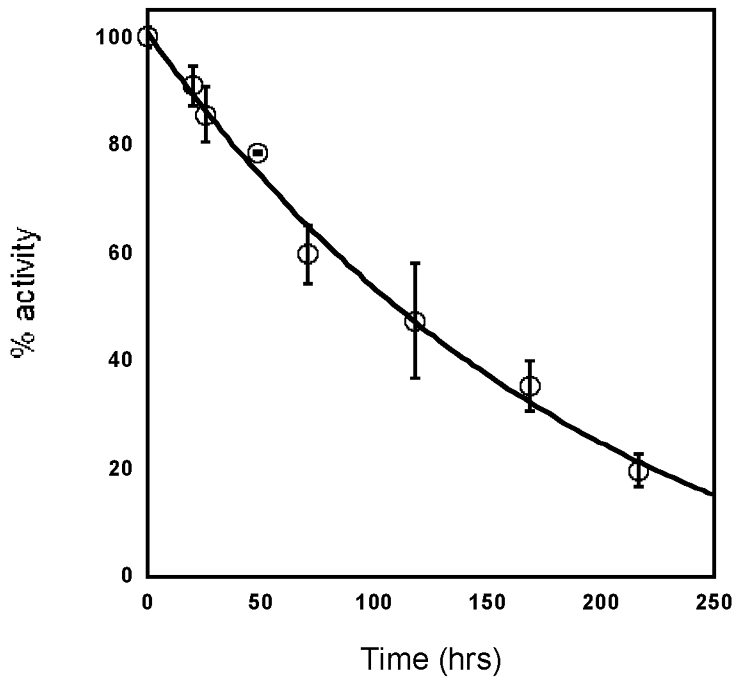
FIG. 3—Activity of PEGylated hCGL-8mut-1 incubated in pooled human serum at 37° C. as a function of time: Apparent $T_{0.5}$=100±4 h.

The serum stability of PEGylated hCGL-8mut-1 was tested by incubation of the enzyme in pooled human serum at 37° C. at a final concentration of 10 µM. At different time points, aliquots were withdrawn and tested for activity using the DTNB assay as described in U.S. Pat. Publ. 2011/0200576, which is incorporated herein by reference in its entirety. After plotting the data, PEGylated hCGL-8mut-1 was calculated to have a half-life ($T_{0.5}$) of 101±4 h (FIG. 3).

Example 9

Pharmacodymanic Analysis of PEGylated hCGL-8Mut-1 in Mice

Figure 4:
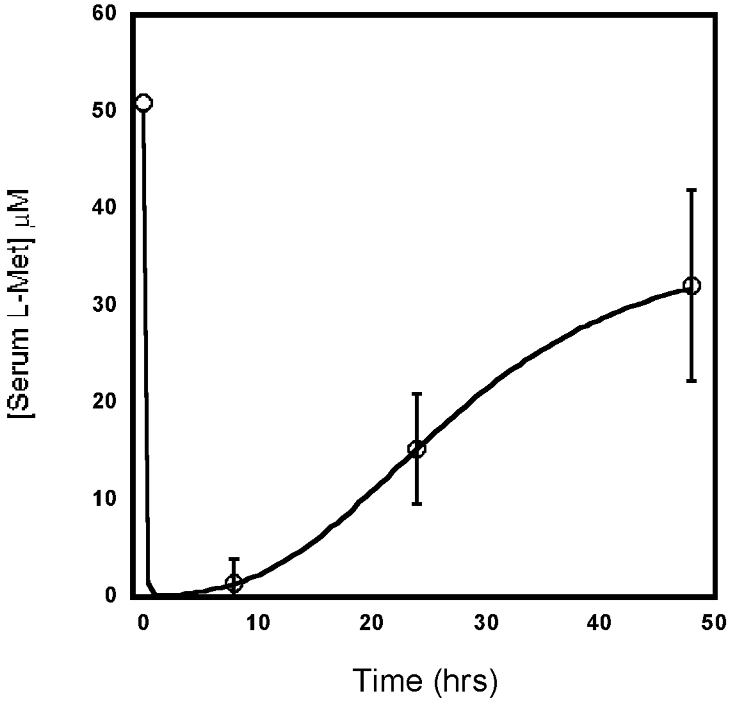
FIG. 4—A single dose of PEG-hCGL-8mut-1 can lower serum L-methionine to therapeutically relevant levels for over 15 h without dietary intervention in a mouse model.
Figure 5:
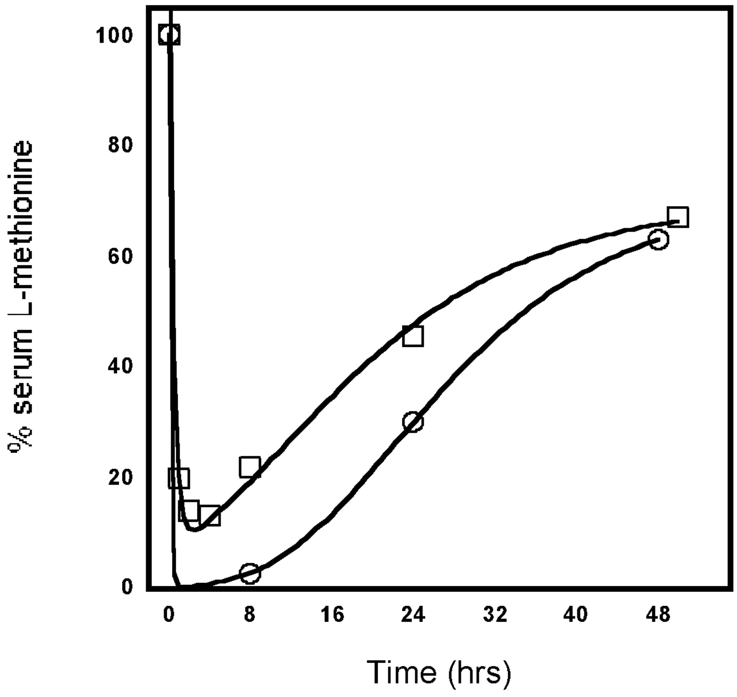
FIG. 5—Comparison of single doses of 200 mg/kg PEG-hCGL-NLV (open square) and 50 mg/kg PEG-hCGL-8mut-1 (open circle) in reducing serum L-methionine in mice on a normal diet.

To assess the efficacy of the engineered human methionine degrading enzymes disclosed in Examples 4-7 above in clearing L-methionine in a mouse model, three groups of three animals each were administered 50 mg/kg of PEG-hCGL-8mut-1 by tail vein injection, while being maintained on a normal diet. Groups were sacrificed at time points corresponding to 8, 24, and 48 h by cardiac venipuncture for serum collection. The serum samples were then analyzed for L-methionine content by derivatization with o-phthalaldehyde (OPA) followed by high performance liquid chromatography (HPLC) essentially as described by Agilent Technologies (on the world wide web at chem.agilent.com/Library/datasheets/Public/5980-3088.PDF). This dosing scheme using PEG-hCGL-8mut-1 enabled depletion of L-methionine to levels lower than 5 μM for over 15 h (FIG. 4). In contrast, administration of 200 mg/kg of the PEGylated hCGL-NLV to mice on a normal diet only lowered serum L-methionine to ~10 μM for 4 h (FIG. 5).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005
U.S. Pat. No. 5,824,344
U.S. Pat. No. 5,830,880
U.S. Pat. No. 5,846,945
U.S. Pat. No. 5,889,155
U.S. Pat. No. 8,709,407
U.S. Pat. Publn. 2009/0304666
U.S. Pat. Publn. 2011/0200576
Ashe et al., *Biochem. Biophys. Res. Commun.,* 57:417, 1974.
Austin-Ward and Villaseca, *Revista Medica de Chile,* 126 (7):838-845, 1998.
Ausubel et al., Current Protocols in Molecular Biology, Greene Publishing Associates and Wiley Interscience, N.Y., 1994.
Breillout et al., In: *Methionine dependency of malignant tumors: a possible approach for therapy*, Oxford University Press, 1628-1632, 1990.
Bukowski et al., *Clinical Cancer Res.,* 4(10):2337-2347, 1998.
Christodoulides et al., *Microbiology,* 144(Pt 11):3027-3037, 1998.
Davidson et al., *J. Immunother.,* 21(5):389-398, 1998.
Esaki and Soda, *Methods Enzymol.,* 143: 459, 1987.
Gill and von Hippel, Calculation of protein extinction coefficients from amino acid sequence data. *Anal Biochem,* 182(2):319-326, 1989.
Halpern et al., *Proc. Natl. Acad. Sci.,* 71:1133-1136, 1974.
Hanibuchi et al., *Int. J. Cancer,* 78(4):480-485, 1998.
Harkki et al., *BioTechnology,* 7:596-603, 1989.
Hellstrand et al., *Acta Oncologica,* 37(4):347-353, 1998.
Hollander, *Front. Immun.,* 3:3, 2012.
Hopwood et al., In: *Genetic Manipulation of Streptomyces*, A Laboratory Manual, The John Innes Foundation, Norwich, Conn., 1985.
Hori et al., *Cancer Res.,* 56:2116-2122, 1996.
Hui and Hashimoto, *Infection Immun.,* 66(11):5329-5336, 1998.
Ito et al., *J. Biochem.,* 79:1263, 1976.
Kreis and Goodenow, *Cancer Res.,* 38:2259-2262, 1978.
Kreis et al., *Cancer Res.,* 40:634-641, 1980.
Kreis, *Cancer Treatment Rpts.,* 63:1069, 1979.
Kudou et al., *J. Biochem.,* 141:535, 2007.
Lishko et al., *Anticancer Res.,* 13:1465-1468, 1993.
Lordanescu, *J Bacteriol,* 12:597 601, 1975.
Lu et al., Cloning and nucleotide sequence of human liver cDNA encoding for cystathionine gamma-lyase. *Biochem. Biophys. Res. Comm.,* 189(2): 749-758, 1992.
Maniatis et al., Molecular Cloning, A Laboratory Manual, Cold Spring Harbor Press, Cold Spring Harbor, N.Y., 1988.
Mellor et al., *Gene,* 24:1-14, 1983.
Nakamura et al., *Anal. Biochem.,* 138:421-424, 1984.
Penttila et al., *Gene,* 61:155-164, 1987.
Qin et al., *Proc. Natl. Acad. Sci. USA,* 95(24):14411-14416, 1998.
Rao et al., Role of the Transsulfuration Pathway and of {gamma}-Cystathionase Activity in the Formation of Cysteine and Sulfate from Methionine in Rat Hepatocytes. *Journal of Nutrition,* 120(8):837, 1990.
Remington's Pharmaceutical Sciences, 18th Ed. Mack Printing Company, 1289-1329, 1990.
Sibakov et al., *Eur. J Biochem.,* 145:567 572, 1984.
Sridhar et al., *Acta Crystall. Section D: Biolog, Crystall.,* 56:1665-1667, 2000.
Steegborn et al., Kinetics and inhibition of recombinant human cystathionine gamma-lyase. Toward the rational control of transsulfuration. *Journal of Biological Chemistry,* 274(18):12675, 1999.
Stone et al., De novo engineering of a human cystathionine-Î³-lyase for systemic L-methionine depletion cancer therapy. *ACS Chemical Biology,* 7(11): 1822-1829, 2012.
Takakura et al., Assay method for antitumor L-methionine-lyase: comprehensive kinetic analysis of the complex reaction with L-methionine. *Analytical Biochemistry,* 327 (2):233-240, 2004.
Tan et al., *Anticancer Res.,* 16:3937-3942, 1996a.
Tan et al., *Anticancer Res.,* 16:3931-3936, 1996b.
Tan et al., *Protein Express. Purif.,* 9:233-245, 1997a.

Tan et al., *Anticancer Res.,* 17:3857-3860, 1997b.

Ward, Proc, Embo-Alko Workshop on Molecular Biology of Filamentous Fungi, Helsinki, 119-128, 1989.

Wawrzynczak and Thorpe, In: Immunoconjugates, *Antibody Conuugates In Radioimaging And Therapy Of Cancer*, Vogel (Ed.), NY, Oxford University Press, 28, 1987.

Yang et al., In: *PEGylation confers greatly extended half-life and attenuated immunogenicity to recombinant methioninase in primates*, AACR, 6673-6678, 2004a.

Yang et al., In: *Pharmacokinetics, methionine depletion, and antigenicity of recombinant methioninase in primates*, AACR, 2131-2138, 2004b.

Yoshioka et al., *Cancer Res.,* 58:2583-2587, 1998.

What is claimed is:

1. A nucleic acid comprising a nucleotide sequence encoding a modified human cystathionine-γ-lyase (CGL) enzyme having at least the following substitutions relative to a native human CGL amino acid sequence (see SEQ ID NO: 1), said substitutions selected from (a) E59N, S63L, L91M, R119L, K268R, T311G, E339V and I353S; (b) E59I, S63L, L91M, R119L, K268R, T311G, E339V and I353S; (c) E59N, S63L, L91M, R119A, K268R, T311G, E339V and I353S; and (d) E59I, S63L, L91M, R119A, K268R, T311G, E339V and I353S, wherein the modified human CGL enzyme has higher methionine-γ-lyase activity compared to hMGL-NLV.

2. The nucleic acid of claim 1, wherein the nucleic acid is codon optimized for expression in bacteria, fungus, insects, or mammals.

3. An expression vector comprising the nucleic acid of claim 2.

4. A host cell comprising the nucleic acid of claim 2.

5. The host cell of claim 4, wherein the host cell is a bacterial cell, a fungal cell, an insect cell, or a mammalian cell.

6. The host cell of claim 5, wherein the bacterial cell is an *E. coli* strain having deletions of genes ilvA and metA.

7. The nucleic acid of claim 1, wherein the encoded enzyme has at least the substitutions E59N, S63L, L91M, R119L, K268R, T311G, E339V and I353S.

8. The nucleic acid of claim 1, wherein the encoded enzyme has at least the substitutions E59I, S63L, L91M, R119L, K268R, T311G, E339V and I353 S.

9. The nucleic acid of claim 1, wherein the encoded enzyme has at least the substitutions E59N, S63L, L91M, R119A, K268R, T311G, E339V and I353S.

10. The nucleic acid of claim 1, wherein the encoded enzyme has at least the substitutions E59I, S63L, L91M, R119A, K268R, T311G, E339V and I353S.

11. The nucleic acid of claim 1, wherein the encoded enzyme further comprises a heterologous peptide segment.

12. The nucleic acid of claim 1, wherein the heterologous peptide segment is an XTEN peptide, an IgG Fc, an albumin, or an albumin binding peptide.

* * * * *

UNITED STATES PATENT AND TRADEMARK OFFICE

CERTIFICATE OF CORRECTION

PATENT NO. : 9,624,484 B2
APPLICATION NO. : 15/297102
DATED : April 18, 2017
INVENTOR(S) : George Georgiou et al It is certified that error appears in the above-identified patent and that said Letters Patent is hereby corrected as shown below:

In the Claims

In Claim 12, Column 98, Line 18, delete "1" and replace with --11-- therefor.

Signed and Sealed this
First Day of August, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 26

<210> SEQ ID NO 1
<211> LENGTH: 405
<212> TYPE: PRT
<213> ORGANISM: Homo sapiens

<400> SEQUENCE: 1

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Glu Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320
```

-continued

```
Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 2
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 2

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Asn Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270
```

```
Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 3
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 3

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220
```

Val Ser Val Asn Cys Glu Ser Leu His Asn Arg Leu Arg Phe Leu Gln
225 230 235 240

Asn Ser Leu Gly Ala Val Pro Ser Pro Ile Asp Cys Tyr Leu Cys Asn
245 250 255

Arg Gly Leu Lys Thr Leu His Val Arg Met Glu Arg His Phe Lys Asn
260 265 270

Gly Met Ala Val Ala Gln Phe Leu Glu Ser Asn Pro Trp Val Glu Lys
275 280 285

Val Ile Tyr Pro Gly Leu Pro Ser His Pro Gln His Glu Leu Val Lys
290 295 300

Arg Gln Cys Thr Gly Cys Gly Gly Met Val Thr Phe Tyr Ile Lys Gly
305 310 315 320

Thr Leu Gln His Ala Glu Ile Phe Leu Lys Asn Leu Lys Leu Phe Thr
325 330 335

Leu Ala Val Ser Leu Gly Gly Phe Glu Ser Leu Ala Glu Leu Pro Ala
340 345 350

Ser Met Thr His Ala Ser Val Leu Lys Asn Asp Arg Asp Val Leu Gly
355 360 365

Ile Ser Asp Thr Leu Ile Arg Leu Ser Val Gly Leu Glu Asp Glu Glu
370 375 380

Asp Leu Leu Glu Asp Leu Asp Gln Ala Leu Lys Ala Ala His Pro Pro
385 390 395 400

Ser Gly Ser His Ser
405

<210> SEQ ID NO 4
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 4

Met Gln Glu Lys Asp Ala Ser Ser Gln Gly Phe Leu Pro His Phe Gln
1 5 10 15

His Phe Ala Thr Gln Ala Ile His Val Gly Gln Asp Pro Glu Gln Trp
20 25 30

Thr Ser Arg Ala Val Val Pro Pro Ile Ser Leu Ser Thr Thr Phe Lys
35 40 45

Gln Gly Ala Pro Gly Gln His Ser Gly Phe Ile Tyr Ser Arg Leu Gly
50 55 60

Asn Pro Thr Arg Asn Cys Leu Glu Lys Ala Val Ala Ala Leu Asp Gly
65 70 75 80

Ala Lys Tyr Cys Leu Ala Phe Ala Ser Gly Met Ala Ala Thr Val Thr
85 90 95

Ile Thr His Leu Leu Lys Ala Gly Asp Gln Ile Ile Cys Met Asp Asp
100 105 110

Val Tyr Gly Gly Thr Asn Leu Tyr Phe Arg Gln Val Ala Ser Glu Phe
115 120 125

Gly Leu Lys Ile Ser Phe Val Asp Cys Ser Lys Ile Lys Leu Leu Glu
130 135 140

Ala Ala Ile Thr Pro Glu Thr Lys Leu Val Trp Ile Glu Thr Pro Thr
145 150 155 160

Asn Pro Thr Gln Lys Val Ile Asp Ile Glu Gly Cys Ala His Ile Val
165 170 175

His Lys His Gly Asp Ile Ile Leu Val Val Asp Asn Thr Phe Met Ser
180 185 190

Pro Tyr Phe Gln Arg Pro Leu Ala Leu Gly Ala Asp Ile Ser Met Tyr
195 200 205

Ser Ala Thr Lys Tyr Met Asn Gly His Ser Asp Val Val Met Gly Leu
210 215 220

Val Ser Val Asn Cys Glu Ser Leu His Asn Arg Leu Arg Phe Leu Gln
225 230 235 240

Asn Ser Leu Gly Ala Val Pro Ser Pro Ile Asp Cys Tyr Leu Cys Asn
245 250 255

Arg Gly Leu Lys Thr Leu His Val Arg Met Glu Arg His Phe Lys Asn
260 265 270

Gly Met Ala Val Ala Gln Phe Leu Glu Ser Asn Pro Trp Val Glu Lys
275 280 285

Val Ile Tyr Pro Gly Leu Pro Ser His Pro Gln His Glu Leu Val Lys
290 295 300

Arg Gln Cys Thr Gly Cys Gly Gly Met Val Thr Phe Tyr Ile Lys Gly
305 310 315 320

Thr Leu Gln His Ala Glu Ile Phe Leu Lys Asn Leu Lys Leu Phe Thr
325 330 335

Leu Ala Val Ser Leu Gly Gly Phe Glu Ser Leu Ala Glu Leu Pro Ala
340 345 350

Ser Met Thr His Ala Ser Val Leu Lys Asn Asp Arg Asp Val Leu Gly
355 360 365

Ile Ser Asp Thr Leu Ile Arg Leu Ser Val Gly Leu Glu Asp Glu Glu
370 375 380

Asp Leu Leu Glu Asp Leu Asp Gln Ala Leu Lys Ala Ala His Pro Pro
385 390 395 400

Ser Gly Ser His Ser
405

<210> SEQ ID NO 5
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 5

Met Gln Glu Lys Asp Ala Ser Ser Gln Gly Phe Leu Pro His Phe Gln
1 5 10 15

His Phe Ala Thr Gln Ala Ile His Val Gly Gln Asp Pro Glu Gln Trp
20 25 30

Thr Ser Arg Ala Val Val Pro Pro Ile Ser Leu Ser Thr Thr Phe Lys
35 40 45

Gln Gly Ala Pro Gly Gln His Ser Gly Phe Asn Tyr Ser Arg Leu Gly
50 55 60

Asn Pro Thr Arg Asn Cys Leu Glu Lys Ala Val Ala Ala Leu Asp Gly
65 70 75 80

Ala Lys Tyr Cys Leu Ala Phe Ala Ser Gly Met Ala Ala Thr Val Thr
85 90 95

Ile Thr His Leu Leu Lys Ala Gly Asp Gln Ile Ile Cys Met Asp Asp
100 105 110

Val Tyr Gly Gly Thr Asn Ala Tyr Phe Arg Gln Val Ala Ser Glu Phe
115 120 125

```
Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 6
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 6

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80
```

-continued

```
Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 7
<211> LENGTH: 405
<212> TYPE: PRT
<213> ORGANISM: Pongo abelii

<400> SEQUENCE: 7

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Pro Ile Ser Pro Ser Val Thr Phe Lys
        35                  40                  45
```

```
Gln Gly Ala Pro Gly Gln His Ser Gly Phe Val Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Ala Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Val Glu Leu Pro Ala
            340                 345                 350

Val Met Thr His Ala Ser Val Leu Lys Lys Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 8
<211> LENGTH: 405
<212> TYPE: PRT
<213> ORGANISM: Macaca fascicularis

<400> SEQUENCE: 8

Met Gln Glu Lys Asp Ala Ser Ser Gln Gly Phe Leu Pro His Phe Gln
```

-continued

```
1               5                   10                  15

His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
        35                  40                  45

Gln Ala Ala Pro Gly Gln His Ser Gly Phe Glu Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Gly Val Glu Lys
        275                 280                 285

Val Ile Tyr Pro Gly Leu Pro Ser His Pro Gln His Glu Leu Ala Lys
    290                 295                 300

Arg Gln Cys Thr Gly Cys Thr Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Val Glu Leu Pro Ala
            340                 345                 350

Ile Met Thr His Ala Ser Val Pro Lys Asn Asp Arg Asp Val Leu Gly
        355                 360                 365

Ile Ser Asp Thr Leu Ile Arg Leu Ser Val Gly Leu Glu Asp Glu Lys
    370                 375                 380

Asp Leu Leu Glu Asp Leu Asp Gln Ala Leu Lys Ala Ala His Pro Pro
385                 390                 395                 400

Ser Gly Ser His Asn
                405
```

<210> SEQ ID NO 9

<211> LENGTH: 405
<212> TYPE: PRT
<213> ORGANISM: Pan troglodytes

<400> SEQUENCE: 9

Met Gln Glu Lys Asp Ala Ser Ser Gln Gly Phe Leu Pro His Phe Gln
1 5 10 15

His Phe Ala Thr Gln Ala Ile His Val Gly Gln Asp Pro Glu Gln Trp
20 25 30

Thr Ser Arg Ala Leu Val Pro Pro Ile Ser Leu Ser Thr Thr Phe Lys
35 40 45

Gln Gly Ala Pro Gly Gln His Ser Gly Phe Glu Tyr Ser Arg Ser Gly
50 55 60

Asn Pro Thr Arg Asn Cys Leu Glu Lys Ala Val Ala Ala Leu Asp Gly
65 70 75 80

Ala Lys Tyr Cys Leu Ala Phe Ala Ser Gly Leu Ala Ala Thr Val Thr
85 90 95

Ile Thr His Leu Leu Lys Ala Gly Asp Gln Ile Ile Cys Met Asp Asp
100 105 110

Val Tyr Gly Gly Thr Asn Arg Tyr Phe Arg Gln Val Ala Ser Glu Phe
115 120 125

Gly Leu Lys Ile Ser Phe Val Asp Cys Ser Lys Ile Lys Leu Leu Glu
130 135 140

Ala Ala Ile Thr Pro Glu Thr Lys Leu Val Trp Ile Glu Thr Pro Thr
145 150 155 160

Asn Pro Thr Gln Lys Val Ile Asp Ile Glu Ala Cys Ala His Ile Val
165 170 175

His Lys His Gly Asp Ile Ile Leu Val Val Asp Asn Thr Phe Met Ser
180 185 190

Pro Tyr Phe Gln Arg Pro Leu Ala Leu Gly Ala Asp Ile Cys Met Tyr
195 200 205

Ser Ala Thr Lys Tyr Met Asn Gly His Ser Asp Val Val Met Gly Leu
210 215 220

Val Ser Val Asn Cys Glu Ser Leu His Asn Arg Leu Arg Phe Leu Gln
225 230 235 240

Asn Ser Leu Gly Ala Val Pro Ser Pro Ile Asp Cys Tyr Leu Cys Asn
245 250 255

Arg Gly Leu Lys Thr Leu His Val Arg Met Glu Lys His Phe Lys Asn
260 265 270

Gly Met Ala Val Ala Gln Phe Leu Glu Ser Asn Pro Trp Val Glu Lys
275 280 285

Val Ile Tyr Pro Gly Leu Pro Ser His Pro Gln His Glu Leu Val Lys
290 295 300

Arg Gln Cys Thr Gly Cys Thr Gly Met Val Thr Phe Tyr Ile Lys Gly
305 310 315 320

Thr Leu Gln His Ala Glu Ile Phe Leu Lys Asn Leu Lys Leu Phe Thr
325 330 335

Leu Ala Glu Ser Leu Gly Gly Phe Glu Ser Leu Ala Glu Leu Pro Ala
340 345 350

Ile Met Thr His Ala Ser Val Leu Lys Asn Asp Arg Asp Val Leu Gly
355 360 365

Ile Ser Asp Thr Leu Ile Arg Leu Ser Val Gly Leu Glu Asp Glu Glu
370 375 380

Asp Leu Leu Glu Asp Leu Asp Gln Ala Leu Lys Ala Ala His Pro Pro

```
385                 390                 395                 400

Ser Gly Ser His Ser
                405


<210> SEQ ID NO 10
<211> LENGTH: 405
<212> TYPE: PRT
<213> ORGANISM: Pan paniscus

<400> SEQUENCE: 10

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln His Ser Gly Phe Glu Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Ala Glu Leu Pro Ala
            340                 345                 350
```

```
Ile Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 11
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 11

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Pro Ile Ser Pro Ser Val Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Ala Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300
```

```
Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Leu Lys Lys Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 12
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 12

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Pro Ile Ser Pro Ser Val Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Ala Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255
```

-continued

```
Arg Gly Leu Lys Thr Leu Gln Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Leu Lys Lys Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 13
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 13

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Pro Ile Ser Pro Ser Val Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Ala Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205
```

Ser Ala Thr Lys Tyr Met Asn Gly His Ser Asp Val Val Met Gly Leu
    210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Leu Lys Lys Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 14
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 14

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Pro Ile Ser Pro Ser Val Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Ala Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

```
Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Leu Lys Lys Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 15
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 15

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
        35                  40                  45

Gln Ala Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110
```

```
Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Gly Val Glu Lys
        275                 280                 285

Val Ile Tyr Pro Gly Leu Pro Ser His Pro Gln His Glu Leu Ala Lys
    290                 295                 300

Arg Gln Cys Thr Gly Cys Gly Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Pro Lys Asn Asp Arg Asp Val Leu Gly
        355                 360                 365

Ile Ser Asp Thr Leu Ile Arg Leu Ser Val Gly Leu Glu Asp Glu Lys
    370                 375                 380

Asp Leu Leu Glu Asp Leu Asp Gln Ala Leu Lys Ala Ala His Pro Pro
385                 390                 395                 400

Ser Gly Ser His Asn
                405


<210> SEQ ID NO 16
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 16

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
        35                  40                  45

Gln Ala Ala Pro Gly Gln His Ser Gly Phe Ile Tyr Ser Arg Leu Gly
    50                  55                  60
```

-continued

```
Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Gly Val Glu Lys
        275                 280                 285

Val Ile Tyr Pro Gly Leu Pro Ser His Pro Gln His Glu Leu Ala Lys
    290                 295                 300

Arg Gln Cys Thr Gly Cys Gly Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Pro Lys Asn Asp Arg Asp Val Leu Gly
        355                 360                 365

Ile Ser Asp Thr Leu Ile Arg Leu Ser Val Gly Leu Glu Asp Glu Lys
    370                 375                 380

Asp Leu Leu Glu Asp Leu Asp Gln Ala Leu Lys Ala Ala His Pro Pro
385                 390                 395                 400

Ser Gly Ser His Asn
                405


<210> SEQ ID NO 17
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 17

Met Gln Glu Lys Asp Ala Ser Ser Gln Gly Phe Leu Pro His Phe Gln
1               5                   10                  15
```

-continued

```
His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
        35                  40                  45

Gln Ala Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Gly Val Glu Lys
        275                 280                 285

Val Ile Tyr Pro Gly Leu Pro Ser His Pro Gln His Glu Leu Ala Lys
    290                 295                 300

Arg Gln Cys Thr Gly Cys Gly Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Pro Lys Asn Asp Arg Asp Val Leu Gly
        355                 360                 365

Ile Ser Asp Thr Leu Ile Arg Leu Ser Val Gly Leu Glu Asp Glu Lys
    370                 375                 380

Asp Leu Leu Glu Asp Leu Asp Gln Ala Leu Lys Ala Ala His Pro Pro
385                 390                 395                 400

Ser Gly Ser His Asn
                405
```

<210> SEQ ID NO 18
<211> LENGTH: 405
<212> TYPE: PRT

<213> ORGANISM: Artificial Sequence
<220> FEATURE:
<223> OTHER INFORMATION: Synthetic polypeptide

<400> SEQUENCE: 18

```
Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
        35                  40                  45

Gln Ala Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Gly Val Glu Lys
        275                 280                 285

Val Ile Tyr Pro Gly Leu Pro Ser His Pro Gln His Glu Leu Ala Lys
    290                 295                 300

Arg Gln Cys Thr Gly Cys Gly Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ser Met Thr His Ala Ser Val Pro Lys Asn Asp Arg Asp Val Leu Gly
        355                 360                 365

Ile Ser Asp Thr Leu Ile Arg Leu Ser Val Gly Leu Glu Asp Glu Lys
    370                 375                 380

Asp Leu Leu Glu Asp Leu Asp Gln Ala Leu Lys Ala Ala His Pro Pro
```

-continued 385 390 395 400

Ser Gly Ser His Asn
405

<210> SEQ ID NO 19
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 19

Met Gln Glu Lys Asp Ala Ser Ser Gln Gly Phe Leu Pro His Phe Gln
1 5 10 15

His Phe Ala Thr Gln Ala Ile His Val Gly Gln Asp Pro Glu Gln Trp
20 25 30

Thr Ser Arg Ala Leu Val Pro Pro Ile Ser Leu Ser Thr Thr Phe Lys
35 40 45

Gln Gly Ala Pro Gly Gln His Ser Gly Phe Asn Tyr Ser Arg Leu Gly
50 55 60

Asn Pro Thr Arg Asn Cys Leu Glu Lys Ala Val Ala Ala Leu Asp Gly
65 70 75 80

Ala Lys Tyr Cys Leu Ala Phe Ala Ser Gly Met Ala Ala Thr Val Thr
85 90 95

Ile Thr His Leu Leu Lys Ala Gly Asp Gln Ile Ile Cys Met Asp Asp
100 105 110

Val Tyr Gly Gly Thr Asn Leu Tyr Phe Arg Gln Val Ala Ser Glu Phe
115 120 125

Gly Leu Lys Ile Ser Phe Val Asp Cys Ser Lys Ile Lys Leu Leu Glu
130 135 140

Ala Ala Ile Thr Pro Glu Thr Lys Leu Val Trp Ile Glu Thr Pro Thr
145 150 155 160

Asn Pro Thr Gln Lys Val Ile Asp Ile Glu Ala Cys Ala His Ile Val
165 170 175

His Lys His Gly Asp Ile Ile Leu Val Val Asp Asn Thr Phe Met Ser
180 185 190

Pro Tyr Phe Gln Arg Pro Leu Ala Leu Gly Ala Asp Ile Cys Met Tyr
195 200 205

Ser Ala Thr Lys Tyr Met Asn Gly His Ser Asp Val Val Met Gly Leu
210 215 220

Val Ser Val Asn Cys Glu Ser Leu His Asn Arg Leu Arg Phe Leu Gln
225 230 235 240

Asn Ser Leu Gly Ala Val Pro Ser Pro Ile Asp Cys Tyr Leu Cys Asn
245 250 255

Arg Gly Leu Lys Thr Leu His Val Arg Met Glu Arg His Phe Lys Asn
260 265 270

Gly Met Ala Val Ala Gln Phe Leu Glu Ser Asn Pro Trp Val Glu Lys
275 280 285

Val Ile Tyr Pro Gly Leu Pro Ser His Pro Gln His Glu Leu Val Lys
290 295 300

Arg Gln Cys Thr Gly Cys Gly Gly Met Val Thr Phe Tyr Ile Lys Gly
305 310 315 320

Thr Leu Gln His Ala Glu Ile Phe Leu Lys Asn Leu Lys Leu Phe Thr
325 330 335

Leu Ala Val Ser Leu Gly Gly Phe Glu Ser Leu Ala Glu Leu Pro Ala

```
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 20
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 20

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Leu Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
```

290 295 300

Arg Gln Cys Thr Gly Cys Gly Gly Met Val Thr Phe Tyr Ile Lys Gly
305 310 315 320

Thr Leu Gln His Ala Glu Ile Phe Leu Lys Asn Leu Lys Leu Phe Thr
325 330 335

Leu Ala Val Ser Leu Gly Gly Phe Glu Ser Leu Ala Glu Leu Pro Ala
340 345 350

Ser Met Thr His Ala Ser Val Leu Lys Asn Asp Arg Asp Val Leu Gly
355 360 365

Ile Ser Asp Thr Leu Ile Arg Leu Ser Val Gly Leu Glu Asp Glu Glu
370 375 380

Asp Leu Leu Glu Asp Leu Asp Gln Ala Leu Lys Ala Ala His Pro Pro
385 390 395 400

Ser Gly Ser His Ser
405

<210> SEQ ID NO 21
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 21

Met Gln Glu Lys Asp Ala Ser Ser Gln Gly Phe Leu Pro His Phe Gln
1 5 10 15

His Phe Ala Thr Gln Ala Ile His Val Gly Gln Asp Pro Glu Gln Trp
20 25 30

Thr Ser Arg Ala Leu Val Pro Pro Ile Ser Leu Ser Thr Thr Phe Lys
35 40 45

Gln Gly Ala Pro Gly Gln His Ser Gly Phe Asn Tyr Ser Arg Leu Gly
50 55 60

Asn Pro Thr Arg Asn Cys Leu Glu Lys Ala Val Ala Ala Leu Asp Gly
65 70 75 80

Ala Lys Tyr Cys Leu Ala Phe Ala Ser Gly Met Ala Ala Thr Val Thr
85 90 95

Ile Thr His Leu Leu Lys Ala Gly Asp Gln Ile Ile Cys Met Asp Asp
100 105 110

Val Tyr Gly Gly Thr Asn Ala Tyr Phe Arg Gln Val Ala Ser Glu Phe
115 120 125

Gly Leu Lys Ile Ser Phe Val Asp Cys Ser Lys Ile Lys Leu Leu Glu
130 135 140

Ala Ala Ile Thr Pro Glu Thr Lys Leu Val Trp Ile Glu Thr Pro Thr
145 150 155 160

Asn Pro Thr Gln Lys Val Ile Asp Ile Glu Ala Cys Ala His Ile Val
165 170 175

His Lys His Gly Asp Ile Ile Leu Val Val Asp Asn Thr Phe Met Ser
180 185 190

Pro Tyr Phe Gln Arg Pro Leu Ala Leu Gly Ala Asp Ile Cys Met Tyr
195 200 205

Ser Ala Thr Lys Tyr Met Asn Gly His Ser Asp Val Val Met Gly Leu
210 215 220

Val Ser Val Asn Cys Glu Ser Leu His Asn Arg Leu Arg Phe Leu Gln
225 230 235 240

Asn Ser Leu Gly Ala Val Pro Ser Pro Ile Asp Cys Tyr Leu Cys Asn

```
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 22
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 22

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Leu Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
```

```
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 23
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 23

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln His Ser Gly Phe Asn Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
```

```
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 24
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 24

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
```

```
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 25
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 25

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln His Ser Gly Phe Asn Tyr Ser Arg Leu Gly
```

```
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405


<210> SEQ ID NO 26
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 26

Met Gln Glu Lys Asp Ala Ser Ser Gln Gly Phe Leu Pro His Phe Gln
```

-continued

```
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln His Ser Gly Phe Ile Tyr Ser Arg Leu Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Met Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Ala Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Arg His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Gly Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ser Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
                405
```